(12) United States Patent
Kubota

(10) Patent No.: US 7,182,760 B2
(45) Date of Patent: Feb. 27, 2007

(54) LASER THERAPY METHOD, HIGHLY LASER BEAM-ABSORBING MEDIA TO BE USED IN THE THERAPY AND LASER THERAPY APPARATUS WITH THE USE OF THE SAME

(76) Inventor: Shigehiro Kubota, 67-19, Saimyoji, Shimokaiinji, Nagaokakyo-shi, Kyoto (JP) 617-0845

( * ) Notice: Subject to any disclaimer, the term of this patent is extended or adjusted under 35 U.S.C. 154(b) by 112 days.

(21) Appl. No.: 10/415,334

(22) PCT Filed: Oct. 30, 2001

(86) PCT No.: PCT/JP01/09528
§ 371 (c)(1),
(2), (4) Date: Apr. 29, 2003

(87) PCT Pub. No.: WO02/36201
PCT Pub. Date: May 10, 2002

(65) Prior Publication Data
US 2004/0030369 A1 Feb. 12, 2004

(30) Foreign Application Priority Data
Oct. 31, 2000 (JP) .............................. 2000-332386
Mar. 1, 2001 (JP) .............................. 2001-56894

(51) Int. Cl.
*A61B 18/22* (2006.01)

(52) U.S. Cl. .............................. 606/15; 606/16; 606/13
(58) Field of Classification Search .............. 606/9–16; 385/123
See application file for complete search history.

(56) References Cited
U.S. PATENT DOCUMENTS

| 4,846,172 A | * | 7/1989 | Berlin ........................... 606/4 |
| 4,959,063 A | | 9/1990 | Kojima |
| 4,998,930 A | * | 3/1991 | Lundahl ....................... 606/15 |
| 5,203,780 A | * | 4/1993 | Liebler ......................... 606/14 |

(Continued)

FOREIGN PATENT DOCUMENTS
GB WO 92/00106 * 9/1992

(Continued)

*Primary Examiner*—Roy D. Gibson
(74) *Attorney, Agent, or Firm*—Wenderoth, Lind & Ponack, L.L.P.

(57) ABSTRACT

The present invention relates to a laser treatment method and a laser treatment apparatus which can cause thermal damage, such as evaporation or necrosis due to coagulation of organic tissue which is to be subjected to thermal damage, in a sure manner regardless of an absorption percentage of laser beam due to a color tone or composition of the organic tissue, thereby enabling diffusion of cancer cells, due to an abnormally high pressure from evaporation of diseased tissue or the like, to be prevented. The laser treatment method and the laser treatment apparatus have a configuration wherein a laser beam absorption medium is injected between diseased tissue, which is to be an object of laser irradiation, and a laser beam output end, and a laser beam is cast onto the aforementioned laser beam absorption medium so as to cause thermal damage such as evaporation or coagulation of the aforementioned diseased tissue which is the object of laser irradiation, and furthermore, in an event of an abnormal pressure occurring due to evaporation of the diseased tissue, this pressure is vented externally.

14 Claims, 15 Drawing Sheets

U.S. PATENT DOCUMENTS

| | | | |
|---|---|---|---|
| 5,520,680 A * | 5/1996 | Shapshay et al. | 606/12 |
| 5,569,240 A | 10/1996 | Dowlatshahi et al. | |
| 5,571,098 A * | 11/1996 | Domankevitz et al. | 606/15 |
| 5,843,071 A * | 12/1998 | Bath | 606/6 |
| 6,343,174 B1 * | 1/2002 | Neuberger | 385/123 |
| 6,464,694 B1 * | 10/2002 | Massengill | 606/15 |
| 2002/0045890 A1 * | 4/2002 | Celliers et al. | 606/7 |

FOREIGN PATENT DOCUMENTS

| | | |
|---|---|---|
| JP | 63-238860 | 10/1988 |
| JP | 64-17638 | 1/1989 |
| JP | 1-170451 | 7/1989 |
| JP | 7-100144 | 4/1995 |
| JP | 8-133977 | 5/1996 |
| JP | 2525655 | 11/1996 |
| JP | 9-10222 | 1/1997 |
| JP | 9-173346 | 7/1997 |
| JP | 9-266955 | 10/1997 |
| JP | 10-71212 | 3/1998 |
| JP | 2983561 | 9/1999 |
| JP | 3082123 | 6/2000 |
| JP | 2001-218772 | 8/2001 |
| WO | 94/26184 | 11/1994 |

* cited by examiner

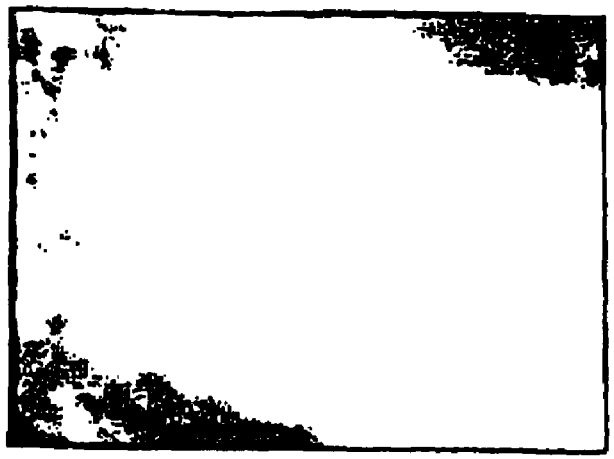
Fig.10(c) INJECTION 40 cc/h
Fig.10(b) INJECTION (+) 20 cc/h
Fig.10(a) INJECTION (−)

| | INJECTION (-) | INJECTION (20 cc/h) | INJECTION (40 cc/h) | INJECTION (50 cc/h) |
|---|---|---|---|---|
| COAGULATION (mm) | 7×14 | 10×15 | 14×20 | 15×20 |
| CAVITY (mm) | 2×7 | 2.5×6 | – | – |
| CARBONIZATION | + | + | – | – |

10W

13W

15W

SINGLE INJECTION OF 1 cc OF 20% DILUTED BLOOD
COAGULATION (mm)   24 × 24
CAVITY (mm)        16 × 16

SINGLE INJECTION OF 0.5 cc OF 20% DILUTED BLOOD
COAGULATION (mm)   12 × 20
CAVITY (mm)        4 × 7

Fig.14
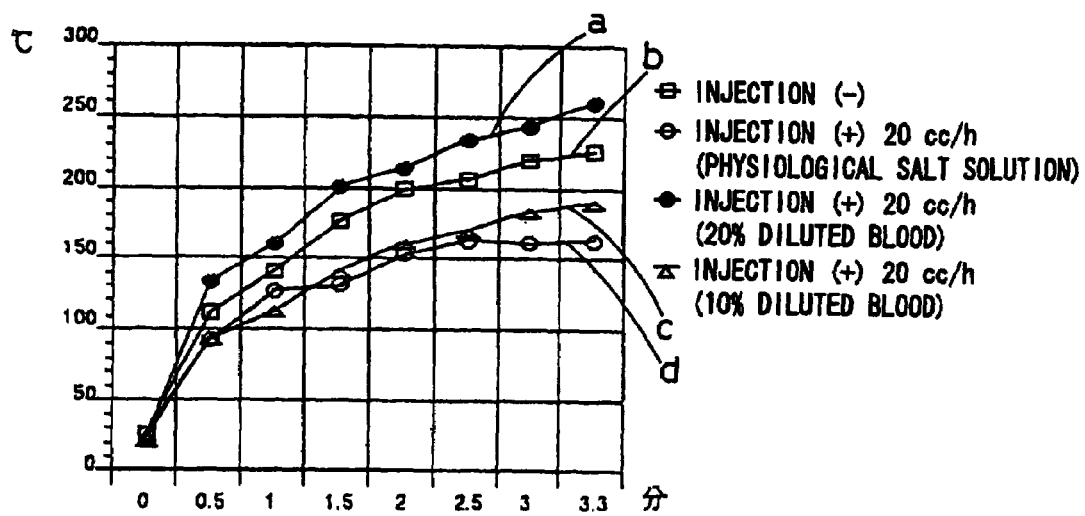
|  | INJECTION (−) | INJECTION (+) 20 cc/h (PHYSIOLOGICAL SALT SOLUTION) | INJECTION (+) 20 cc/h (20% DILUTED BLOOD) | INJECTION (+) 20 cc/h (10% DILUTED BLOOD) |
|---|---|---|---|---|
| COAGULATION (mm) | 7×14 | 14×20 | 14×17 | 12×12 |
| CAVITY (mm) | 2×7 | − | 8×13 | 6×10 |
| CARBONIZATION | + | − | + | + |
Fig.15(a)　　　Fig.15(b)
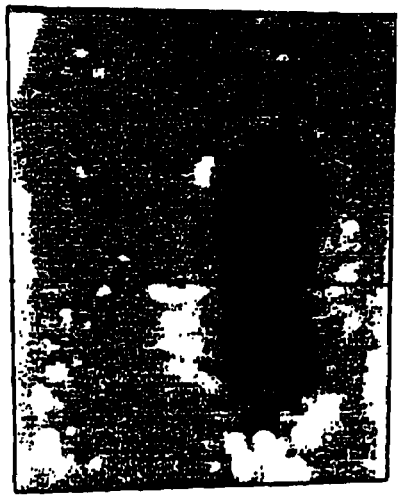
1 cc
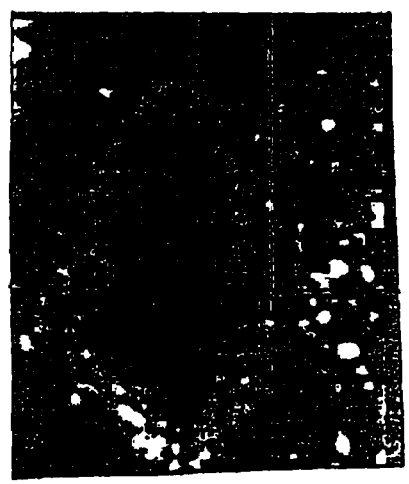
2 cc Fig.18
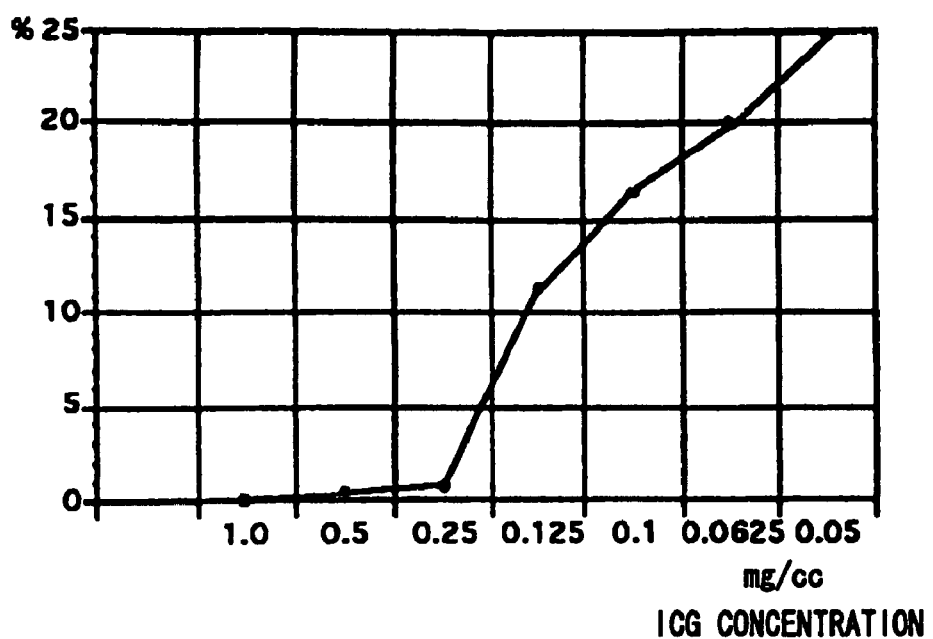
ICG CONCENTRATION
Fig.19(a)      Fig.19(b)      Fig.19(c)
 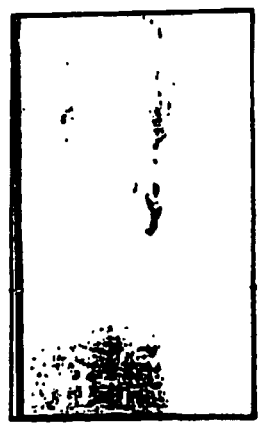 

LASER THERAPY METHOD, HIGHLY LASER BEAM-ABSORBING MEDIA TO BE USED IN THE THERAPY AND LASER THERAPY APPARATUS WITH THE USE OF THE SAME

This application is a National Stage application of PCT/JP01/09528, filed Oct. 30, 2001.

TECHNICAL FIELD

The present invention relates to a laser treatment which causes evaporation, coagulation, and necrosis of organic tissue in a sure manner, and particularly to a laser treatment method which can be used not only for malignant solid tumors but also for benign solid tumors, a laser-absorbing medium having high absorbance of laser light (hereinafter referred to as laser-absorbing medium) for the aforementioned treatment, and a laser treatment apparatus using the aforementioned treatment and medium.

BACKGROUND ART

Conventionally, laser treatment apparatuses have been provided wherein a laser beam is cast onto diseased tissue, which is a diseased portion, so as to cause thermal damage such as evaporation, coagulation, or the like, of organic tissue which is the diseased portion, due to energy of the laser beam, thereby performing a laser treatment.

With conventional treatment methods using the laser treatment apparatuses, in order to obtain massive effects of coagulation and necrosis, fiber chips, diffusers, and the like have been used for diffusing a laser beam, or multiple laser beams have been cast at the same time with multiple fibers using a coupler for obtaining an effect as much as possible with regard to coagulation and necrosis.

However, with conventional laser treatment methods, an absorption percentage depends upon a color tone or composition of organic tissue, and accordingly, a degree of thermal damage depends thereupon, and consequently, all internal organs cannot be subjected to conventional laser treatments, and also, it is needless to say that effects are uncertain.

The present invention has been made in order to solve the above-described problems, and it is an object thereof to provide a revolutionary laser treatment method which can cause thermal damage of necrosis due to evaporation or coagulation of tissue, which is to be subjected to thermal damage, in a sure manner regardless of an absorption percentage for a laser beam due to a color tone or composition of organic tissue, a laser-absorbing medium for the aforementioned treatment, and a laser treatment apparatus using the aforementioned treatment and medium.

SUMMARY OF THE INVENTION

In order to realize the above-described object, according to the present invention, a laser-absorbing medium is injected between diseased tissue, which is an object of laser irradiation, and a laser beam output end, and a laser beam is cast onto the aforementioned laser-absorbing medium, so as to cause thermal damage such as evaporation or coagulation of the aforementioned diseased tissue which is the object of laser irradiation.

Furthermore, a laser-absorbing medium is injected between diseased tissue, which is an object of laser irradiation, and a laser beam output end, and a laser beam is cast onto the aforementioned laser-absorbing medium so as to cause thermal damage such as evaporation or coagulation of the aforementioned diseased tissue which is the object of laser irradiation, and in an event of abnormal pressure occurring due to evaporation of the aforementioned diseased tissue, the aforementioned pressure is externally vented.

The aforementioned laser-absorbing medium is injected by a single injection, or in a continuous manner into the aforementioned diseased tissue which is the object of laser irradiation.

An output, administrating quantity of heat, and injecting speed of the aforementioned laser-absorbing medium are controlled corresponding to a size or shape of the aforementioned diseased tissue which is the object of laser irradiation.

A laser-absorbing medium used in the laser treatment method according to the present invention is diluted blood from a patient, indocyanine green, a solution where human serum is added into an indocyanine green solution, a solution where indocyanine green is dissolved in distilled water, or the like.

The present invention comprises a medium injecting device for injecting a laser-absorbing medium into diseased tissue, which is an object of laser irradiation, and a laser beam irradiation device for casting a laser beam onto the aforementioned diseased tissue which is the object of laser irradiation, into which the aforementioned laser-absorbing medium has been injected. The aforementioned medium injecting device comprises a needle for injecting the aforementioned laser-absorbing medium into the aforementioned diseased tissue which is the object of laser irradiation, and a syringe pump for storing the aforementioned laser-absorbing medium therein, which is communicably connected to the aforementioned needle through a connecting portion provided at a rear end portion thereof. The aforementioned laser beam irradiation device comprises a light guide member for guiding a laser beam from a laser beam irradiation device to the aforementioned diseased tissue which is the object of laser irradiation.

The needle is provided with an inserting opening that passes through the aforementioned needle along an axial direction from a front end up to a rear end thereof for inserting the aforementioned light guide member of the aforementioned laser beam irradiation device, an injecting channel that passes through the aforementioned needle is provided in a thick portion between an outer circumference of the aforementioned inserting opening and an inner circumference of the aforementioned needle along the axial direction from the front end up to the rear end of the aforementioned needle, and the aforementioned channel is communicably connected to the aforementioned syringe pump through the aforementioned connecting portion of the aforementioned needle.

Furthermore, the aforementioned needle includes an inserting opening that passes through the aforementioned needle along the axial direction from the front end up to the rear end thereof for inserting a light guide member of the aforementioned laser beam irradiation device, and an outer tube having a thickness, which defines an outer circumference of the aforementioned inserting opening, whereby the aforementioned needle is configured in a shape of a tube. An injecting opening that passes through the aforementioned needle is provided in the portion with a thickness of the aforementioned outer tube along the axial direction from the front end up to the rear end thereof, and is communicably connected to the aforementioned syringe pump through the aforementioned connecting portion of the aforementioned needle, and a seal member is provided at the rear end portion of the aforementioned needle for sealing a gap between the aforementioned inserting opening and the aforementioned light guide member.

The needle comprises an inner tube having an inserting opening for inserting the aforementioned light guide member of the aforementioned laser beam irradiation device, which is provided by passing through the aforementioned needle along the axial direction from the front end up to the rear end thereof, and an outer tube which is detachably mounted to an outer circumference of the aforementioned inner tube, whereby the aforementioned needle is configured in the shape of a tube, and multiple grooves are provided in an outer circumferential wall face of the aforementioned inner tube along the axial direction from a front end up to a rear end of the aforementioned inner tube. Injecting channels for injecting the aforementioned laser-absorbing medium are formed by an inner circumferential wall face of the aforementioned outer tube and the aforementioned grooves on the aforementioned outer-face wall face of the aforementioned inner tube, with the aforementioned inner tube being mounted in the aforementioned outer tube. The aforementioned injecting channels are communicably connected to the aforementioned syringe pump through the aforementioned connecting portion of the aforementioned needle, and a seal member is provided at a rear end portion of the aforementioned needle for sealing a gap between the aforementioned inserting opening and the aforementioned light guide member.

The needle includes a guide portion at the rear end portion of the aforementioned needle, which is communicably connected to the aforementioned inserting opening, for guiding pressure inside the aforementioned inserting opening out from the aforementioned needle, and further comprises a detecting device for detecting the pressure inside the aforementioned inserting opening, along with a pressure adjusting device for adjusting pressure inside the aforementioned inserting opening by guiding pressure externally from the aforementioned guide portion according to pressure detected by the aforementioned detecting device.

The present invention further comprises a gas injecting device which is communicably connected to the aforementioned injecting opening that passes through the aforementioned needle along the axial direction from the front end up to the rear end thereof, for injecting gas externally into the aforementioned injecting opening.

BRIEF DESCRIPTION OF THE DRAWINGS

FIGS. 10(a)–10(c) show explanatory diagrams which illustrate visually-observable views wherein, with the laser treatment method, a 10-W Nd:YAG laser is turned on and off at intervals of 0.5 seconds so as to perform intermittent irradiation with a total administrating quantity of 1000 J;

FIG. 14 is a chart which indicates a temperature change with regard to a concentration of diluted blood used in the laser treatment method;

FIGS. 15(a) and 15(b) show explanatory views which illustrate visually-observably views wherein, with the laser treatment method, following injection of 1 cc or 2 cc of human serum and an indocyanine green solution with a concentration of 0.125 mg/ml by single injection, a 10-W Nd:YAG laser is turned on and off at intervals of 0.5 seconds so as to perform intermittent irradiation with a total administrating quantity of 1000 J;

FIG. 18 is a chart which indicates transmittivity of a indocyanine green solution for a semiconductor laser beam;

FIGS. 19(a)–19(c) show explanatory views which illustrate visually-observable views wherein, with the laser treatment method, a semiconductor laser is turned on and off at intervals of 0.5 seconds so as to perform intermittent irradiation with a total administrating quantity of 1000 J with or without continuous injection of an indocyanine green solution with a concentration of 0.125 mg/ml dissolved in serum and dissolved water;

DETAILED DESCRIPTION OF THE PREFERRED EMBODIMENTS

Description will be made in detail below regarding a laser treatment method according to the present invention, a laser-absorbing medium used for the aforementioned treatment, and a laser treatment apparatus employing the aforementioned treatment method and laser-absorbing medium, with reference to the drawings.

Embodiment 1

With a laser treatment method according to the present invention, a laser-absorbing medium is injected between diseased tissue, which is an object of laser irradiation, and a laser beam output end, and a laser beam is cast onto the laser-absorbing medium so as to cause thermal damage to, or evaporation or coagulation of, the aforementioned diseased tissue which is the object of laser irradiation.

With the present invention, while the laser beam is produced from an Nd:Yag laser as a rule, a diode laser may be used. It is needless to say that a far-infrared or mid-infrared laser such as $Co_2$ (10.6 μm), Ho:YAG (approximately 2 μm), or the like may be used.

Upon casting the aforementioned laser beam, evaporation is instantaneously caused from a beginning of irradiation due to the laser beam, whereby a minute cavity is formed in the diseased tissue which is the object of laser irradiation.

Upon the laser-absorbing medium flowing into the cavity, the laser beam is absorbed into the laser-absorbing medium, and consequently, the laser-absorbing medium becomes a high-temperature heat source.

The aforementioned laser-absorbing medium can be injected into the diseased tissue, which is the object of laser irradiation, by a single injection or in a continuous manner. In the event of the latter, the laser-absorbing medium is continuously injected, and becomes a heat source between the diseased tissue and a laser fiber, thereby enabling expansion of the cavity and thermal damage to peripheral tissue to be caused.

Figure 9:
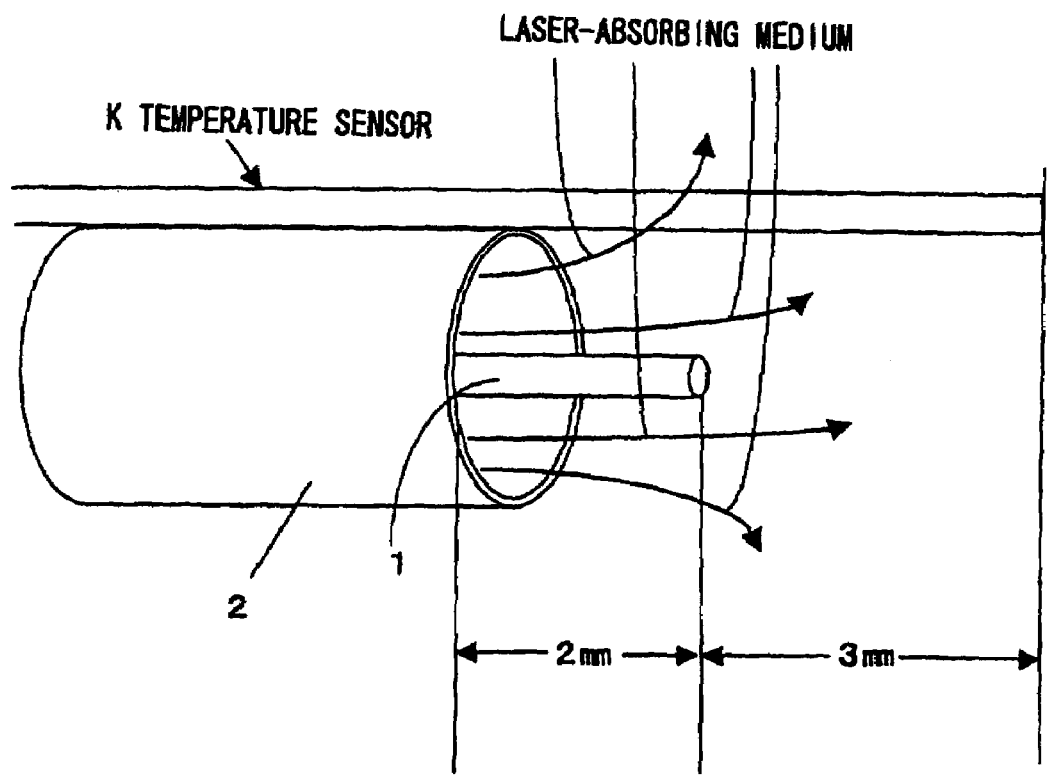
FIG. 9 is an explanatory diagram which illustrates a state wherein, with a laser treatment method, a laser-absorbing medium is injected with an 18-G needle, into which a laser fiber has been inserted, at the same time of laser beam irradiation.

As shown in FIG. 9, the laser-absorbing medium is injected with an 18-G needle 2, into which laser fiber 1 has been inserted, at the same time as laser irradiation.

On the other hand, it is known that continuous injection of a physiological salt solution has cooling effects for a laser beam. FIGS. 10(a)–10(c) illustrate visually-observable views under conditions wherein intermittent irradiation was performed by a 10-W Nd:YAG laser being turned on and off at intervals of 0.5 seconds, with a total administering quantity of 1000 J. As shown in the views, in the event of at least 40 cc/hour of continuous injection of a physiological salt solution, formation of a cavity was not observed (see FIG. 10(c)). Moreover, it was found that in the event of 20 cc/hour of continuous injection of a physiological salt solution, carbonization or coagulation was relatively subdued (see FIG. 10(b)) as compared with a case where injection of the physiological salt solution was not performed (see FIG. 10(a)), and extreme transformation of tissue into fibriform tissue does not readily occur during a restoring process following treatment for an organism.

Figure 11:
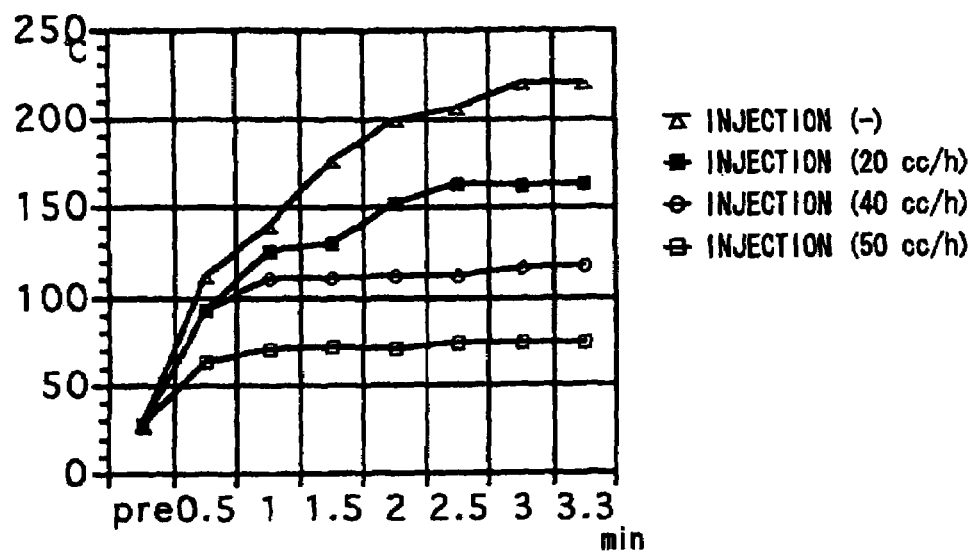
FIG. 11 is a temperature-change chart which indicates thermal damage due to a laser wherein, with a general laser treatment method, a 10-W Nd:YAG laser is turned on and off at intervals of 0.5 seconds so as to perform intermittent irradiation, and injection of at least 40 cc/hour of a physiological salt solution is performed at the same time of laser beam irradiation.

That is to say, with influence of the laser beam upon thermal damage shown in FIG. 11, in a case of intermittent irradiation wherein a 10-W Nd:YAG laser is turned on and off at intervals of 0.5 seconds, in an event of continuously injecting at least 40 cc/hour of a physiological salt solution at the same time as irradiation of a laser beam, evaporation is not caused around a laser-irradiated region. It can be also understood as shown in FIG. 11 that with temperature change at 3 mm from a laser output end of a laser fiber end, the greater an injection quantity of the physiological salt solution is, the greater a cooling effect is. Note that measurement of temperature was performed with a K-thermal sensor.

Figure 12A:
FIGS. 12(a)–12(c) shows explanatory views which illustrate tissue to which visually-observable thermal damage might be caused due to laser output under injection of a physiological salt solution.
Figure 12B:
Figure 12C:

Moreover, it can be understood as shown in FIGS. 12(a)–12(c) that a range of evaporation and coagulation can be controlled from intensity of the laser beam even in an event that conditions of injection quantity and injection speed for the physiological salt solution are the same.

That is to say, intermittent irradiation with various output level of the Nd:YAG laser being turned on and off at intervals of 0.5 seconds was performed, and irradiation of the laser beam with various intensities was performed with a total administrating quantity of 1000 J hour under continuous injection of the physiological salt solution at 40 cc/hour. FIG. 12(a) illustrates a case of a laser beam output of 10 W, FIG. 12(b) illustrates a case of 13 W, and FIG. 12(c) illustrates a case of 15 W. As can be seen from these results, it can be understood that coagulation or formation of a cavity is caused in different manners depending upon laser beam intensity, and the greater the laser beam intensity is, more massive coagulation or formation of a cavity occurs.

Accordingly, with regard to the laser-absorbing medium according to the present invention, it can be understood that thermal damage due to a laser beam theoretically can be controlled by controlling an injection concentration and injection speed thereof.

Thus, with the laser treatment method, the aforementioned laser-absorbing medium can be injected with an output, administrating quantity of heat, and injection speed, being controlled according to a size or shape of diseased tissue which is an object of laser irradiation, and accordingly, a degree of thermal damage applied to the diseased tissue which is the object of laser irradiation can be controlled, thereby enabling a revolutionary treatment in this sort of laser treatment to be realized.

Note that, with the laser treatment method, the laser-absorbing medium used in the aforementioned laser treatment can employ diluted blood from a patient, an indocyanine green solution (ICG), or a solution wherein human serum has been added into an indocyanine green solution (ICG).

Of these, with the diluted blood from the patient, temperature markedly rises due to a great number of red corpuscles, and this temperature rise is markedly different as compared with a case wherein injection of diluted blood from a patient has not been performed. With an Nd:YAG laser beam, evaporation is instantaneously caused from a beginning of irradiation due to the laser beam, and a cavity is formed in the diseased tissue which is the object of laser irradiation. Upon the diluted blood flowing into the cavity, the laser beam is absorbed into the blood, and consequently, the blood becomes a high-temperature heat source. Upon continuous injection of the diluted blood from the patient, the blood becomes a heat source between the diseased tissue and a laser fiber, and thus, expansion of the cavity and addition of thermal damage to peripheral tissue can be made.

Figure 13B:
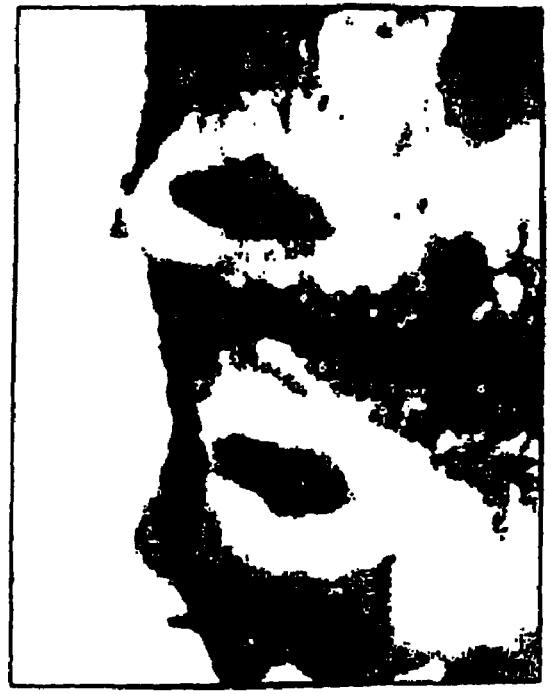
FIGS. 13(a)–13(b) show explanatory views which illustrate visually-observably views wherein, with a laser treatment method, following injection of 0.5 cc or 1 cc of diluted blood with a concentration of 20% into the diseased tissue by single injection, a 10-W Nd:YAG laser is turned on and off at intervals of 0.5 seconds so as to perform intermittent irradiation with a total administrating quantity of 1000 J.
Figure 13A:

FIGS. 13(a) and 13(b) illustrate a treatment example. That is to say, these are visually-observable views wherein following injection 0.5 cc (see FIG. 13(a)) or 1 cc (see FIG. 13(b)) of 20% diluted blood into diseased tissue by a single injection, intermittent irradiation with a 10 W Nd:YAG laser being turned on and off at intervals of 0.5 seconds was performed with a total administrating quantity of 1000 J. As shown in the treatment example, all the injected diluted blood was evaporated after irradiation of the laser beam, and a great degree of necrosis due to coagulation and great size of cavity formation were observed. In the event of injection of 2 cc, a cavity of approximately 2 cc due to evaporation and coagulation of approximately 7 cc were observed. Accordingly, it can be understood that magnitude of coagulation and cavity can be controlled by controlling conditions of laser beam irradiation and injection quantity of diluted blood.

FIG. 14 illustrates temperature change with regard to diseased tissue due to concentration of injected diluted blood, under conditions wherein a 10-W Nd:YAG laser was turned on and off at intervals of 0.5 seconds so as to perform intermittent irradiation with a total administrating quantity of 1000 J. Measurement of temperatures was made with a K-thermal sensor.

With these measurement results, it can be understood that with a temperature change at 3 mm from a laser fiber end, a case of continuously injecting diluted blood of 20% (denoted by reference character "a" in the chart), a case without continuous injection of physiological salt solution (denoted by reference character "b" in the chart), a case of continuously injecting diluted blood of 10% (denoted by reference character "c" in the chart), and a case of continuously injecting a physiological salt solution (denoted by reference character "d" in the chart), exhibit high temperature in that order. A phenomenon wherein the case of continuous injection of 10% diluted blood has a temperature lower than that of the case without continuous injection of the physiological salt solution indicates that a cooling effect due to injection is great, and furthermore, comparing the cases of injection of 10% diluted blood and 20% diluted blood, a temperature in the case with a great number of red corpuscles is higher, and moreover, comparing the case of continuous injection of 20% diluted blood and the case without continuous injection of the physiological salt solution, a temperature rise beyond the cooling effect due to injection is observed.

Overall, it is thought that an Nd:YAG laser beam is absorbed into red corpuscles, and thus the laser beam is converted into thermal energy, that is to say, the red corpuscles introduced between a laser beam output end of the laser fiber end and diseased tissue serve as a heat source.

On the other hand, while it is known that an indocyanine green solution, which is another laser-absorbing medium, has an absorption wavelength of 785 nm, the indocyanine green solution is rapidly connected to serum proteins, and consequently the absorption wavelength becomes 805 nm, and accordingly, absorption of a laser beam from a semiconductor laser with an oscillation wavelength of approximately 805 nm increases. Accordingly, in an event of injecting an indocyanine green solution into which human serum has been added, this becomes a powerful heat source introduced between a laser beam output end and diseased tissue, which is an object of laser irradiation, in the same way as the case of injecting the diluted blood from the patient.

FIGS. 15(a) and 15(b) show visually-observable views wherein following injecting 1 cc (see FIG. 15(a)) or 2 cc (see FIG. 15(b)) of an indocyanine green solution of 0.125 mg/ml, where indocyanine green is added into human serum, into diseased tissue by a single injection, a semiconductor laser of 10 W was turned on and off at intervals of 0.5 seconds so as to perform intermittent irradiation with a total administrating quantity of 1000 J.

In an event of injection of a solution wherein an indocyanine green has been dissolved in distilled water, a temperature at 3 mm from a laser fiber end instantaneously becomes an extremely high temperature immediately after laser beam irradiation, and subsequently, the temperature becomes 74 to 1110° C. This phenomenon is apparent from FIG. 16 and FIG. 17, as well.

Figure 16:
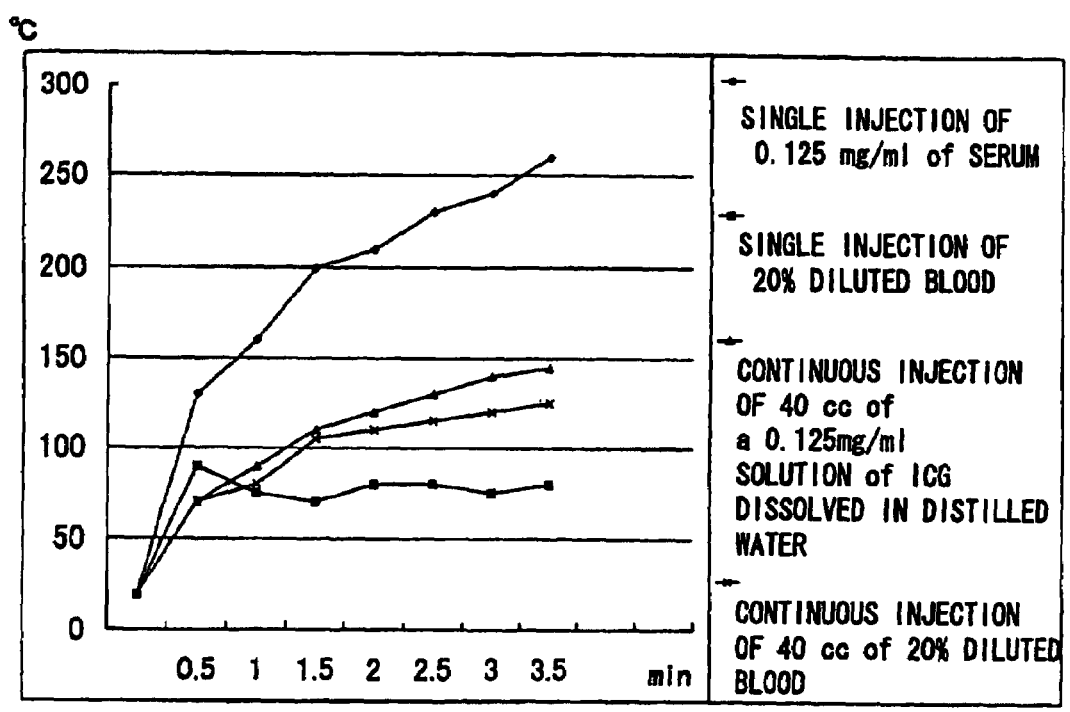
FIG. 16 is a chart which indicates a temperature change wherein, with the laser treatment method, following injection of 1 cc of an indocyanine green solution with a concentration of 0.125 mg/ml dissolved in serum and distilled water by single injection, a 10-W Nd:YAG laser is turned on and off at intervals of 0.5 seconds so as to perform intermittent irradiation with a total administrating quantity of 1000 J while 40 cc of an indocyanine green solution with a concentration of 0.125 mg/ml dissolved in only distilled water is continuously injected at the time of laser irradiation.
Figure 17:
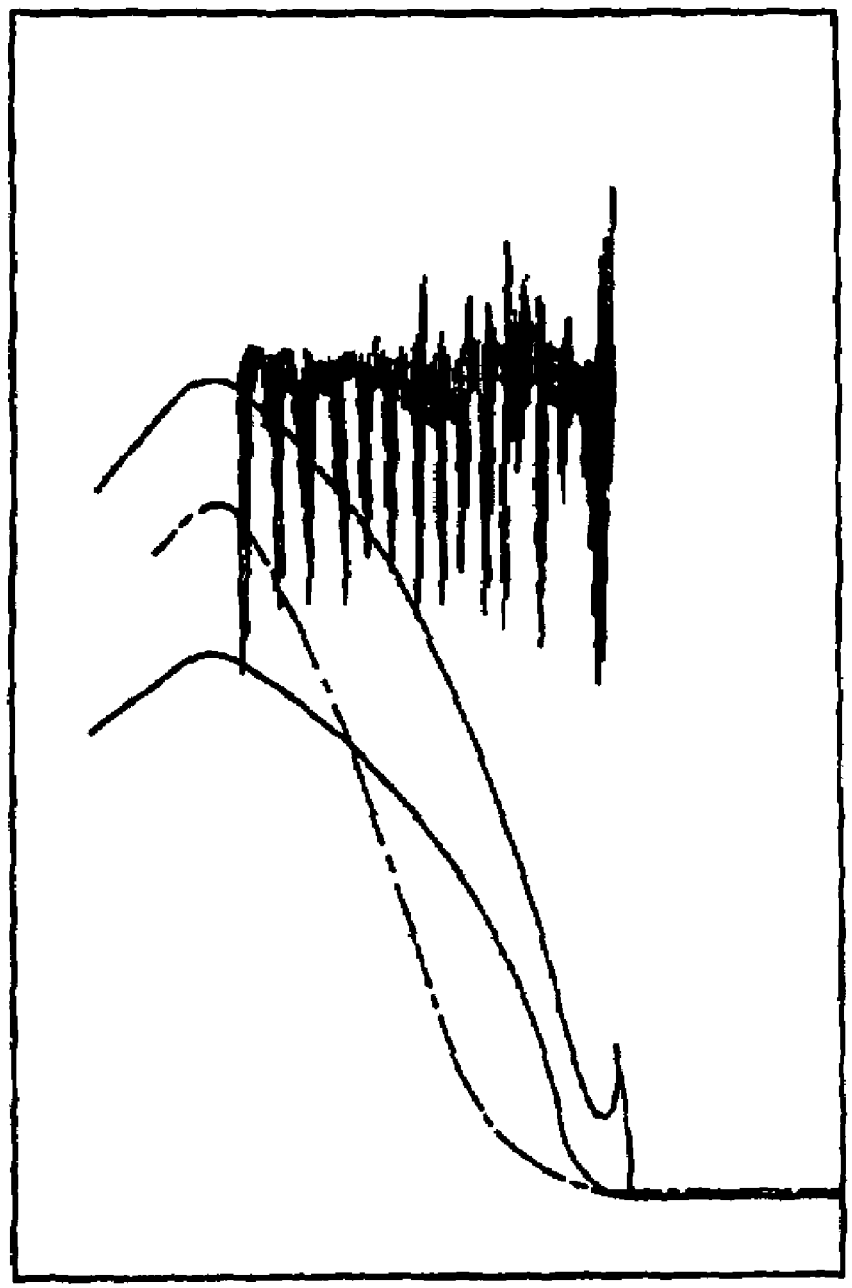
FIG. 17 shows experimental data under the same conditions as in FIG. 16.

FIG. 16 and FIG. 17 are diagrams wherein a temperature change, in a case that following 1 cc of an indocyanine green solution of 0.125 mg/ml, where indocyanine green has been dissolved in serum and distilled water, being injected by a single injection, a semiconductor laser of 10 W was turned on and off at intervals of 0.5 seconds so as to perform intermittent irradiation with a total administrating quantity of 1000 J while continuously injecting 40 cc of a indocyanine green solution of 0.125 mg/ml where indocyanine green has been dissolved in only distilled water. A measurement of temperatures was also made with a K-thermal sensor.

As shown in the drawings, in both of the case that following injecting 1 cc of an indocyanine green solution of 0.125 mg/ml, wherein indocyanine green has been dissolved in serum and distilled water, the semiconductor laser beam was irradiated, and the case wherein following continuously injecting 20% diluted blood, the semiconductor laser was irradiated, gradual rise of temperature can be observed at 3 mm from a laser fiber end.

However, in an event that following continuously injecting 40 cc of an indocyanine green solution with a concentration of 0.125 mg/ml dissolved in only distilled water, the aforementioned laser beam was irradiated, instantaneous rise of the temperature was observed during 0.5 seconds of laser irradiation; however, the temperature, which had temporarily rose, immediately fell during a following pause of laser irradiation, and in practice, a sawtooth temperature change occurred in the range between 62° C. and 105° C.

As described above, a reason that the temperature change occurred in the aforementioned predetermined range of the temperature in spite of measurement of the temperature at a fixed point 3 mm from the laser fiber end, is that the indocyanine green, which is a laser-absorbing medium, absorbed the laser beam, and thus served as a stable heat source.

Moreover, a reason that a formed cavity expands following semiconductor laser irradiation is thought to be that during an extremely initial stage immediately following semiconductor laser irradiation, evaporation due to the semiconductor laser occurs, and accordingly, a cavity is formed and tissue destruction occurs, and subsequently, globulin within the diseased tissue flows into the cavity and connects with the indocyanine green, or the indocyanine green penetrates into the diseased tissue and rapidly reacts with the globulin within the tissue, and subsequently, the indocyanine green with an absorption wavelength of 805 nm absorbs a maximal photo-energy of the semiconductor laser beam, and consequently, thermal destruction of tissue is caused, and cavity expansion is accompanied by a laser-irradiation face receding and expanding, and furthermore, similar processes are repeated, and consequently, a larger cavity and coagulation are formed.

Note that, as shown in FIG. 18, transmittivity of an indocyanine green solution with a concentration of 0.125 mg/ml dissolved in only distilled water as to a diode laser beam is approximately 12%, and the laser beam from the diode laser passes through the indocyanine green solution injected into the cavity, and photo-energy of the laser beam is absorbed into the indocyanine green on a face of tissue in contact with the cavity. Thus, the tissue is thermally destroyed, and the cavity is expanded.

FIGS. 19(a)–19(c) illustrate visually-observable views wherein a semiconductor laser was turned on and off at intervals of 0.5 seconds so as to perform intermittent irradiation with a total administrating quantity of 1000 J with or without continuous injection of an indocyanine green solution with a concentration of 0.125 mg/ml dissolved in serum and distilled water. FIG. 19(a) illustrates an example of a cavity of 2×6 mm accompanied by carbonization and coagulation of 9×16 mm in a case of not performing injection, FIG. 19(b) illustrates an example of formation of a cavity of 3×8 mm not accompanied by carbonization and coagulation of 10×18 mm in a case of continuous injection of 10 cc/hour of an indocyanine green solution with a concentration of 0.125 mg/ml dissolved in distilled water, and FIG. 19(c) illustrates an example of a cavity of 6×9 mm not accompanied by carbonization and coagulation of 14×14 mm in a case of continuous injection of 15 cc/hour of the indocyanine green solution.

Figure 20:
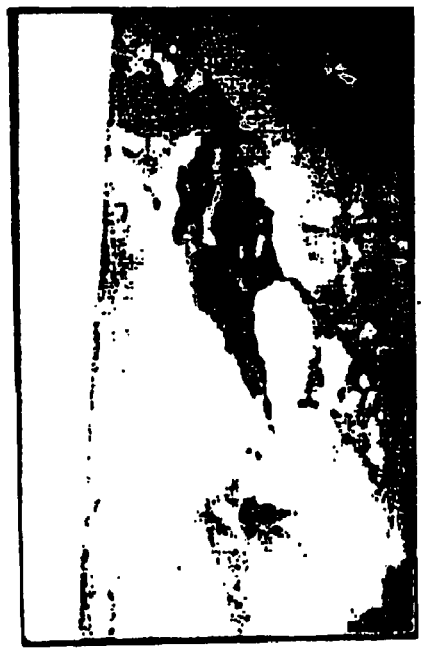
FIG. 20 is an explanatory view which illustrates a visually-observable view wherein, with the laser treatment method, a semiconductor laser of 40 W is turned on and off at intervals of 0.5 seconds so as to perform intermittent irradiation with a total administrating quantity of 500 J under continuous injection of 20 cc of an indocyanine green solution with a concentration of 0.125 mg/ml.

FIG. 20 illustrates a visually-observable view wherein a semiconductor laser of 40 W is turned on and off at intervals of 0.5 seconds so as to perform intermittent irradiation with a total administrating quantity of 500 J under continuous injection of 20 cc of an indocyanine green solution with a concentration of 0.125 mg/ml. As shown in this figure, a large cavity of 2.3×3.7 mm is shown, and a thin layer of coagulation with thickness of 2 to 5 mm is observed around the cavity, and while carbonization occurs, the layer is extremely thin and is not hard. This phenomenon suggests that with evaporation by laser irradiation, the indocyanine green solution with an absorption wavelength of 805 nm is rapidly connected to globulin within tissue and efficiently absorbs the laser beam, and consequently, thermal damage is caused to the tissue.

Figure 21A:
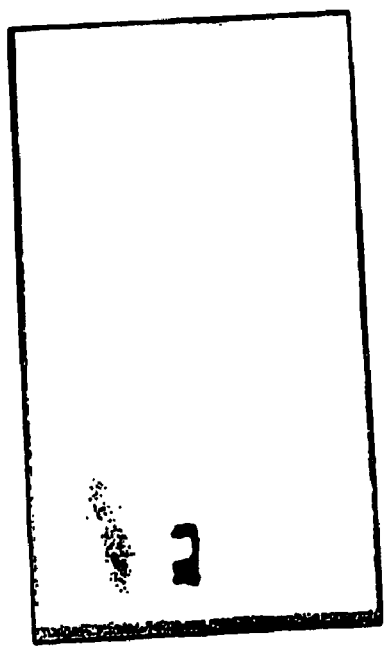
FIGS. 21(a) and 21(b) show comparison views which illustrate a comparison between an example of Indigo, which is a treatment instrument for enlargement of the prostate, and a case wherein a semiconductor laser of 40 W is turned on and off at intervals of 0.5 seconds so as to perform intermittent irradiation with a total administrating quantity of 500 J under continuous injection of 20 cc of an indocyanine green solution with a concentration of 0.125 mg/ml, with the laser treatment method.
Figure 21B:
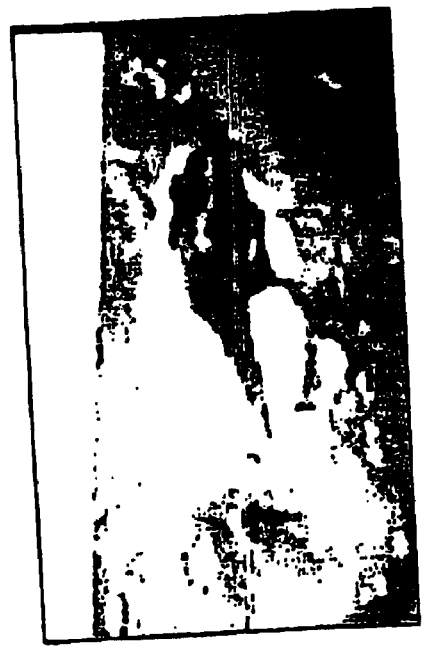

FIGS. 21(a) and 21(b) illustrate a comparison between an example of Indigo (brand name) which is a treatment instrument for enlargement of the prostate, and a case wherein a semiconductor laser of 40 W is turned on and off at intervals of 0.5 seconds so as to perform intermittent irradiation with a total administrating quantity of 500 J under continuous injection of 20 cc of an indocyanine green solution with a concentration of 0.125 mg/ml. With Indigo, which is a treatment instrument for enlargement of the prostate using a semiconductor laser, data has been claimed that one instance of irradiation causes approximately 5 cc of coagulation for pork flesh. FIG. 21(a) illustrates a case of the Indigo wherein administration of 1729 J was made for poultry flesh, and little change was observed. However, a laser probe is designed so as to cast a laser in an elliptical shape. FIG. 21(b) illustrates a visually-observable view of a case under conditions shown in FIG. 20.

As described above, with the laser treatment method, desired cavity and coagulation can be obtained by irradiating a laser beam onto diseased tissue, which is to be subjected to thermal damage, with laser output, administrating quantity of heat, and injection speed and injection quantity of a laser-absorbing medium being controlled, regardless of an absorption percentage for the laser beam due to a color tone of the diseased tissue.

Note that, with the above-described laser treatment method, the kinds of laser and laser-absorbing medium for use are not restricted, so long as an oscillation wavelength of the laser is generally close to a laser beam absorption wavelength of the laser-absorbing medium, and furthermore, any arrangement may be made, so long as the oscillation wavelength of the laser and a maximal absorption wavelength are approximately equal to one another.

Figure 4:
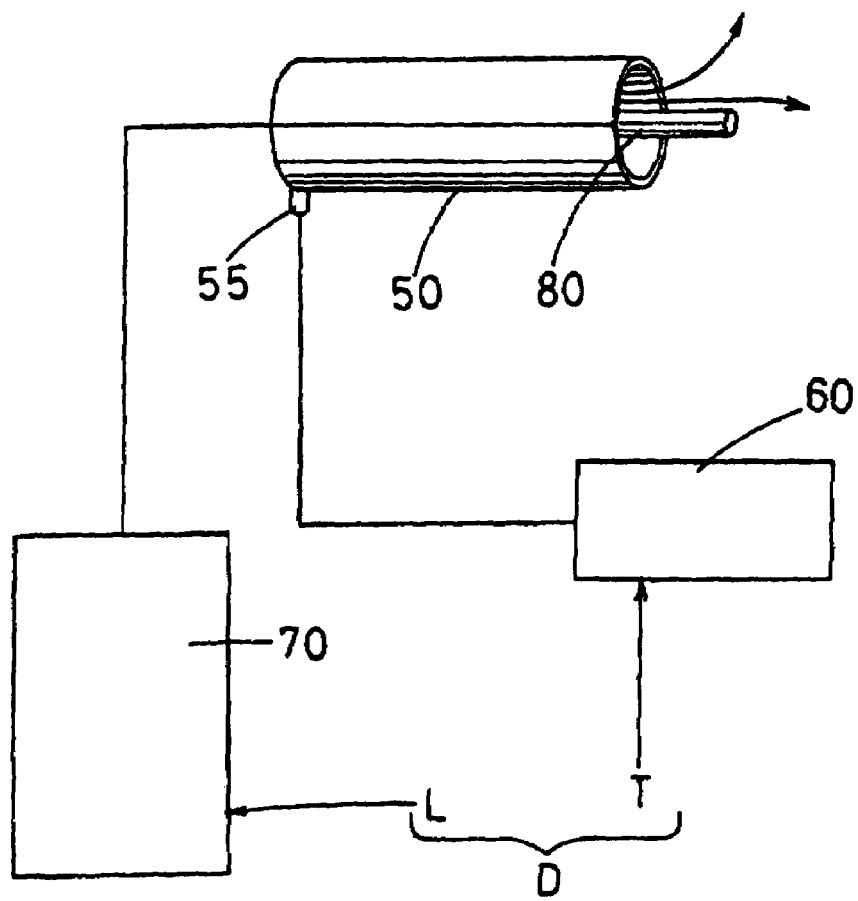
FIG. 4 is a configuration diagram which illustrates a basic configuration of a conventional laser treatment apparatus.

Referring to FIG. 4, description will be made below regarding a laser treatment apparatus for performing the above-described laser treatment method.

As shown in FIG. 4, a laser treatment apparatus D comprises a medium injecting device T for injecting a laser-absorbing medium into diseased tissue, and a laser beam irradiating device L for casting a laser beam onto the diseased tissue into which the aforementioned laser-absorbing medium has been injected.

The aforementioned medium injecting device T comprises a needle 50 for injecting the laser-absorbing medium for absorbing the laser beam in the diseased tissue, and a syringe pump 60 which is communicably connected to the needle 50 through a connecting portion 55 provided at a rear end portion of the needle 50, and the aforementioned laser-absorbing medium is stored in the syringe pomp 60.

On the other hand, the laser beam irradiation device L comprises a laser beam irradiation device 70 for casting a laser beam, and a light guide member 80 for guiding the laser beam cast from the laser beam irradiation device 70 to the diseased tissue, and specifically, a diode laser device or an Nd:YAG laser device is employed as the laser beam irradiation device, and a laser fiber is employed as the light guide member.

With the laser treatment apparatus D having a configuration described above, injection of the laser-absorbing medium is made with the needle 50, into which a laser fiber 80 has been inserted, at the same time as laser beam irradiation.

Specifically, the laser treatment apparatus D has a configuration wherein the laser fiber 80 is inserted into an inner tube of the needle 50, and the laser-absorbing medium is supplied into the needle 50 through the connecting portion 55, provided at the rear end portion of the needle 50, from the external syringe pump 60 so that the laser-absorbing medium is injected into the diseased tissue which is an object of laser beam irradiation, at the same time as laser beam irradiation.

With the laser treatment apparatus having such a configuration, thermal damage such as evaporation or necrosis due to coagulation can be caused in a sure manner to the tissue, which is to be subjected to thermal damage, regardless of an absorption percentage of the laser beam due to a color tone or composition of this organic tissue.

As described above, the laser treatment method and the laser treatment apparatus according to the present invention have a great advantage in that thermal damage such as evaporation or necrosis due to coagulation can be caused in a sure manner to tissue which is to be subjected to thermal damage.

Figure 5:
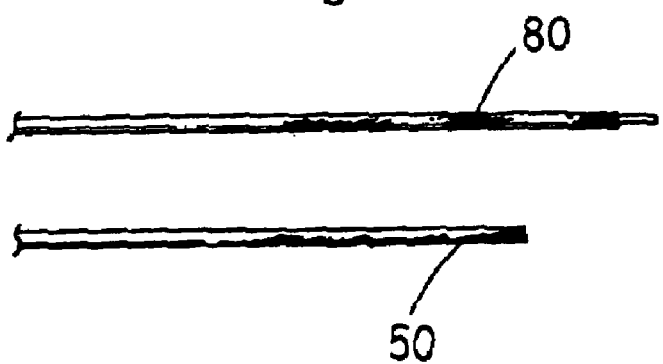
FIG. 5 is an explanatory diagram which illustrates thermal damage caused to a needle and laser fiber of the conventional laser treatment apparatus.

However, with the above-described laser treatment method and the laser treatment apparatus, vapor with high temperature occurs due to evaporation of organic tissue by laser beam irradiation, and accordingly, as shown in FIG. 5, the needle 50 and the laser fiber 80 might be subjected to thermal damage.

Figure 6A:
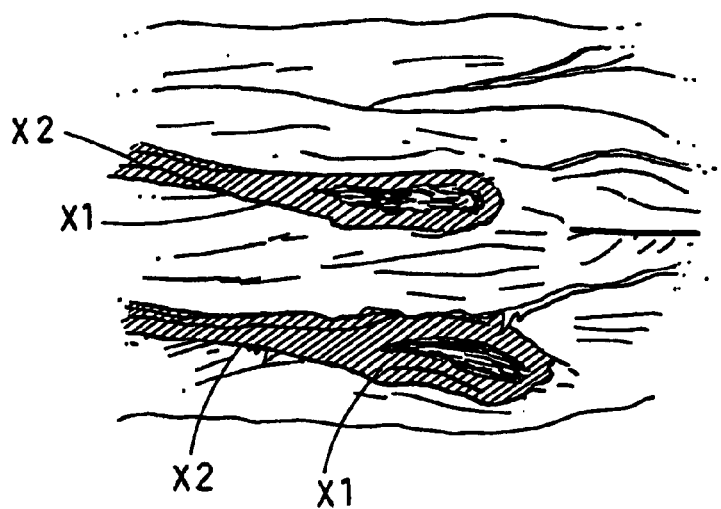
FIGS. 6(a)–6(c) show explanatory diagrams which illustrate thermal damage due to an abnormal rising of pressure from evaporation in an event of using the conventional laser treatment apparatus.
Figure 6B:
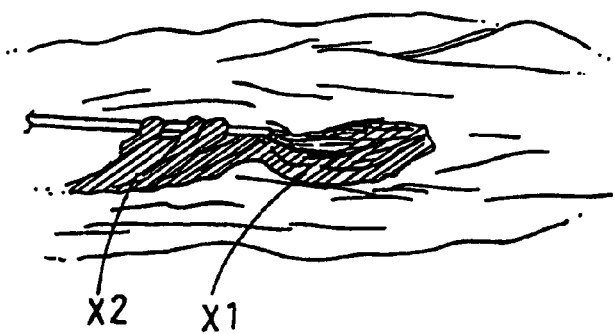

Moreover, as indicated by reference character X2 in FIG. 6(a) and FIG. 6(b), organic tissue around the needle 50 might be subjected to thermal damage due to a backward flow of the vapor with high temperature within the needle 50 or along the needle 50.

Note that, in the drawings, reference character X1 denotes normal thermal damage to the organic tissue in an event of performing laser treatment.

Furthermore, in an event of performing laser treatment for cancer or the like, cancer cells might diffuse due to abnormal rising of pressure from evaporation, and moreover, in some cases, in an event that hard coagulation of the organic tissue occurs around the needle 50 due to laser beam irradiation, vapor with high temperature from evaporation leaks from weak portions in the organic tissue, and consequently, unexpected thermal damage might be caused to the organic tissue, and in a worst-case scenario, damage accompanied by explosion might be caused to the organic tissue.

Now, there is a need to leak pressure of the vapor in order to prevent thermal damage to normal organic tissue due to the vapor with an abnormally high temperature at the time of aforementioned laser beam irradiation; however, with a configuration simply providing a pressure-leaking opening in the needle 50, the laser-absorbing medium leaks and falls from the aforementioned pressure-leaking opening.

Furthermore, there is a need to maintain some pressure in order to expand thermal damage to diseased tissue from pressure due to evaporation, and confirm a degree of damage to the diseased tissue due to an opto-acoustic effect, besides the above-described reasons.

With the laser treatment described above, while the laser-absorbing medium is injected between the diseased tissue, which is the object of laser irradiation, and the laser beam output end, and the laser beam is cast onto the laser-absorbing medium so as to cause thermal damage such as evaporation or coagulation to the aforementioned diseased tissue which is the object of laser irradiation, in an event of the above-described abnormal pressure occurring due to evaporation, there is a need to leak the pressure externally from the diseased tissue.

Accordingly, an embodiment described below has a configuration wherein abnormal pressure is leaked externally in order to protect normal organic tissue and the laser treatment apparatus from a backward flow of vapor with an abnormally high temperature due to evaporation at a time of laser beam irradiation, and also prevent harmful effects such as diffusion of cancer cells or the like from abnormally high pressure due to evaporation of diseased tissue.

Note that, in the description below, a laser beam treatment and a laser treatment apparatus according to a second embodiment have the same basic principle and configuration as the configuration of the above-described laser treatment method and laser treatment apparatus, so same components are denoted by same reference characters, description thereof will be omitted, and description will be made in detail regarding only essential portions of the second embodiment.

Embodiment 2

A laser treatment method according to the second embodiment is characterized by processes wherein following a laser-absorbing medium being injected between diseased tissue, which is an object of laser irradiation, and a laser beam output end, a laser beam is cast onto the aforementioned laser-absorbing medium so as to cause thermal damage such as evaporation or coagulation to the aforementioned diseased tissue which is the object of laser irradiation, and furthermore, in an event of abnormal pressure occurring due to evaporation of the diseased tissue, pressure is leaked externally.

Description will be made below regarding a configuration example for performing the aforementioned laser treatment method with reference to the drawings.

Figure 1A:
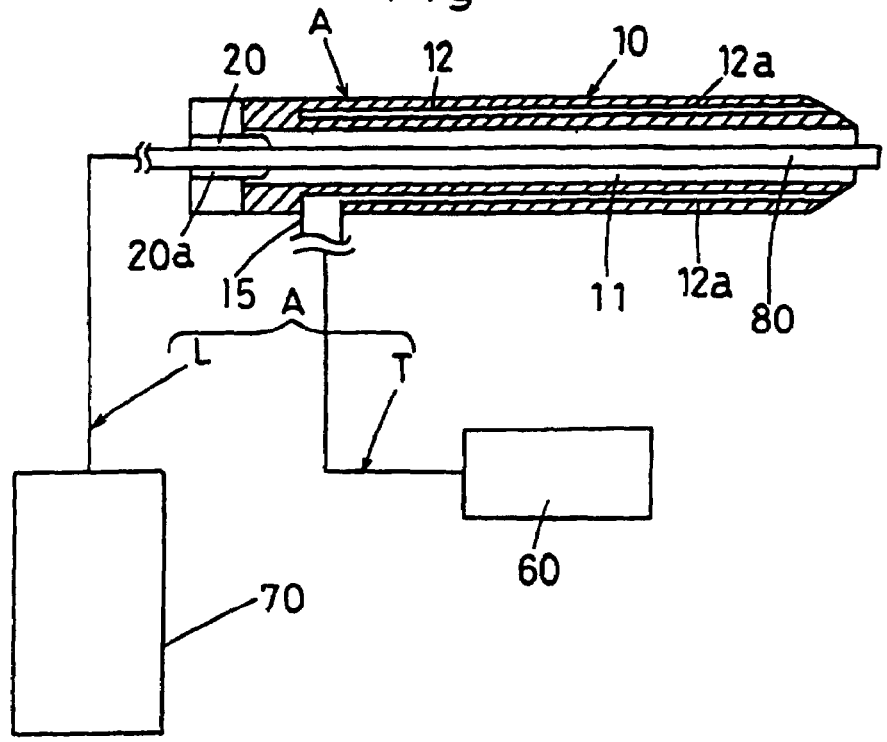
FIGS. 1(a)–1(c) show configuration diagrams which illustrate a basic configuration of a laser treatment apparatus according to the present invention, and a diagram which illustrates a configuration of a needle used in the laser treatment apparatus.

FIG. 1(a) is a configuration diagram which illustrates a basic configuration example of a laser treatment apparatus, and as shown in this figure, a laser treatment apparatus A has a needle 10 for injecting a laser-absorbing medium into diseased tissue, which has a configuration greatly different from that of the needle 50 of the laser treatment apparatus D described above.

Figure 1B:
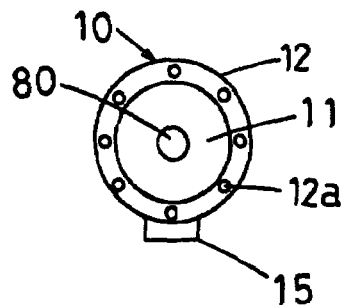

That is to say, as shown in FIGS. 1(a) and 1(b), the aforementioned needle 10 is formed cylindrically and comprises an inserting opening 11 provided so as to insert the needle 10 from a front end up to a rear end thereof along an axial direction thereof, and an outer tube 12, which defines an outer circumference of the aforementioned inserting opening 11, formed in a shape of a tube with a thickness.

A laser fiber 80 is inserted into the inserting opening 11 of the needle 10 as a light guide member for laser beam irradiation apparatus L, and with the present embodiment, a puncture needle of 14-G to 18-G is employed as the needle 10, and a laser fiber of 400 μm or 600 μm is employed as the laser fiber 80.

Note that a decision as to whether either a laser fiber of 400 μm or 600 μm is employed, is made depending upon a size or shape of diseased tissue which is to be an object of laser irradiation.

Furthermore, multiple inserting openings 12a are provided in the outer tube 12 of the needle 10 so as to pass therethrough along an axial direction thereof from a front end up to a rear end thereof, with a configuration wherein rear ends of the aforementioned inserting openings 12a are communicably connected to a connecting portion 15 provided at a rear end portion of the needle 10.

Thus, the aforementioned inserting openings 12a are communicably connected to syringe pump 60 through the connecting portion 15, and in an event of laser beam irradiation, laser-absorbing medium stored within the syringe pump 60 flows into the inserting openings 12a, thereby injecting the laser-absorbing medium into diseased tissue.

Furthermore, a seal member 20 is detachably provided at the rear end portion of the aforementioned needle 10 for sealing a gap between the aforementioned inserting opening 11 and the laser fiber 80 inserted into the aforementioned inserting opening 11. The seal member 20 is a stopper (cap) made of rubber or silicone, and is provided with an inserting opening 20a for inserting the laser fiber 80 along an axial direction thereof.

Thus, the laser fiber 80 is inserted into the inserting opening 20a of the aforementioned seal member 20 so as to be disposed within the inserting opening 11 of the needle 10, and accordingly, the gap between the inserting opening 11 and the laser fiber 80 is sealed with the seal member 20.

Figure 1C:
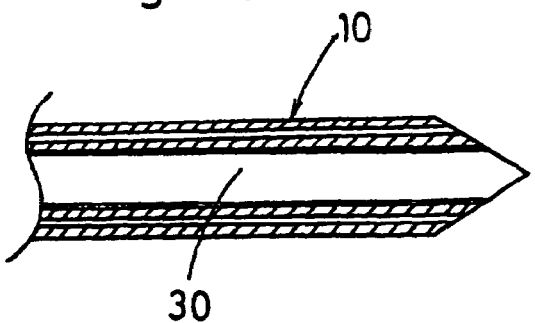

In an event of casting a laser beam using the laser treatment apparatus A which has been provided with the needle 10 having a configuration described above, first of all, as shown in FIG. 1(c), an inner tube 30 is inserted into the inserting opening 11 of the needle 10, and organic tissue is punctured with the needle in this state. Upon the needle 10 reaching diseased tissue, which is an object of laser beam irradiation, the laser fiber 80 is inserted into the inserting opening 11 of the needle 10 so as to cast a laser beam at the same time as injection of a laser-absorbing medium into the diseased tissue.

At this time, as described above, in an event that vapor with an abnormally high pressure occurs due to evaporation from laser irradiation, the high pressure due to the aforementioned evaporation can be vented from the inserting opening 20a of the seal member 20 through the inserting opening 11 of the needle 10, thereby enabling diffusion of cancer cells within organic tissue, or the like, to be prevented, for example.

Also, even in an event of backward flow of vapor with high temperature occurring in the inserting opening 11 of the needle 10, a laser-absorbing medium continuously flows into the injecting openings 12a of the needle 10, and accordingly, the needle itself is cooled, and thus, there is an advantage of preventing thermal damage to the needle 10 or the laser fiber 80 due to the vapor with the high temperature. Furthermore, burns can be prevented from occurring on organic tissue around the needle 10.

Moreover, in an event that necrosis due to coagulation is caused locally on organic tissue at the time of the laser irradiation, malfunction of injection of a laser-absorbing medium is caused at the aforementioned portion; however, the multiple injecting openings 12a are provided in the aforementioned needle 10, and accordingly, malfunction of injection of the laser-absorbing medium can be prevented, and also a greater quantity of the laser-absorbing medium can be diffused into the organic tissue, and the laser-absorbing medium can be efficiently injected into the organic tissue, as compared with a case with only one injecting opening.

The laser treatment apparatus A according to the above-described present embodiment is particularly effective in a case wherein organic tissue is soft and absorption of a laser beam is great. That is to say, in such a case, a cavity formed due to evaporation of the organic tissue by laser beam irradiation becomes large, and backward flow of vapor within the needle 10 decreases.

However, in a case of organic tissue being dense and solid, and absorption of a laser beam being poor, a size of a cavity formed due to evaporation of the organic tissue is small, and accordingly, pressure of vapor due to evaporation rises. Moreover, pressure required for causing thermal damage to a greater extent to diseased tissue is different depending upon each diseased tissue which is an object of laser beam irradiation, and accordingly, there is a need to adjust pressure at a time of laser beam irradiation in order to solve these problems.

Therefore, an embodiment described below includes a pressure adjusting device for adjusting required pressure at a time of laser beam irradiation, and also, for adjusting pressure by guiding the pressure outward in an event that abnormal rising of vapor pressure occurs due to evaporation.

Figure 2:
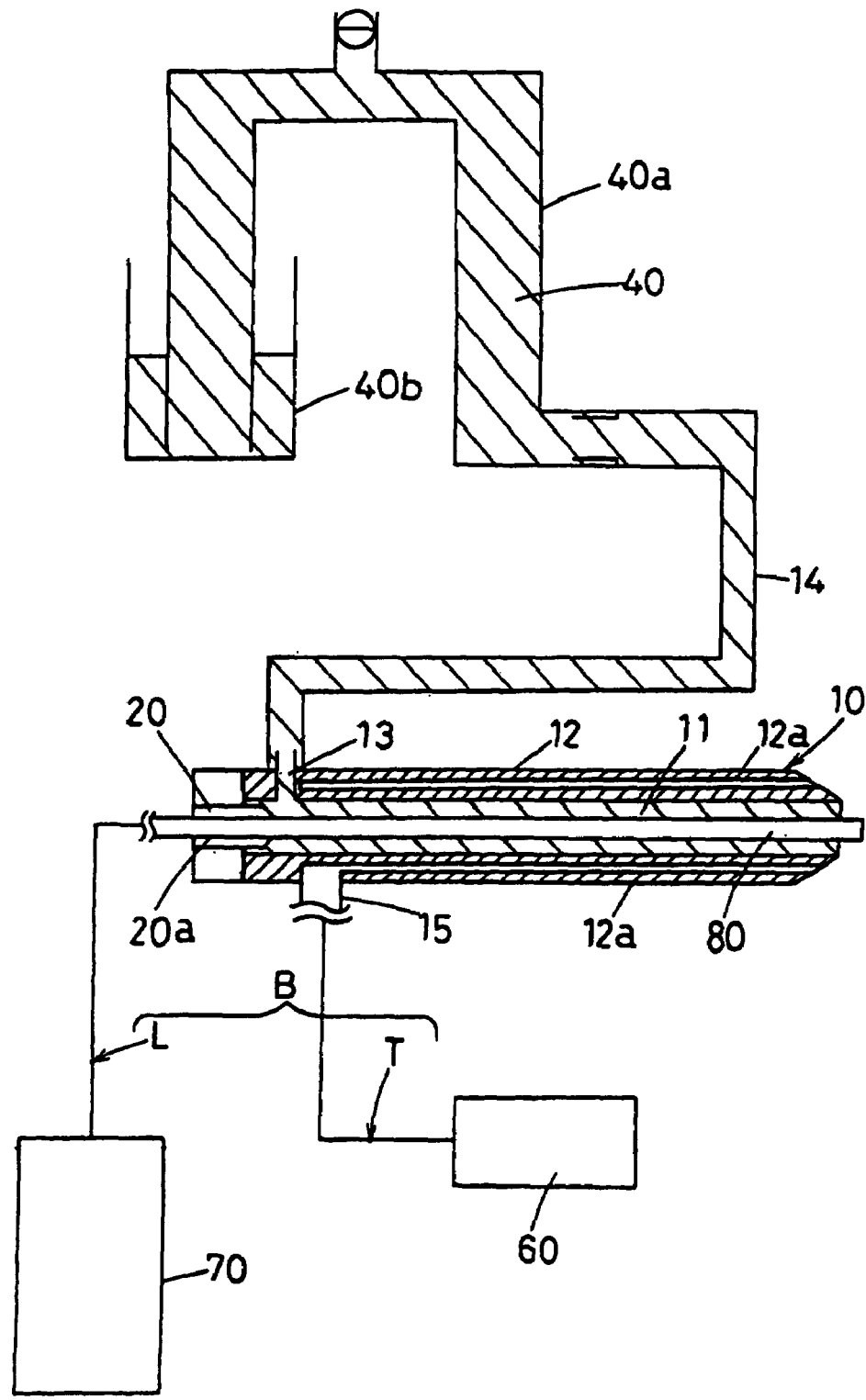
FIG. 2 is a configuration diagram which illustrates another configuration of a laser treatment apparatus according to the present invention.

As shown in FIG. 2, a laser treatment apparatus B according to this present embodiment comprises a guide opening 13 at a rear end portion of the needle 10 of the above-described laser treatment apparatus for venting pressure, and a pressure adjustment device 40 which is communicably connected to the aforementioned guide opening 13.

The aforementioned guide opening 13 is provided at the rear end portion of the needle 10 so as to communicate with inserting opening 11 of the needle 10, and the pressure adjusting device 40 is communicably connected to the aforementioned guide opening 13 through a tube 14.

With the present embodiment, a piston-type pressure adjuster, of which an interior has been filled up with water, is used as the aforementioned pressure adjusting device 40 for adjusting pressure, and the aforementioned pressure adjusting device 40, the tube 14, and the inserting opening 11 of the needle 10, are filled with water by being communicably connected one to another.

As shown in FIG. 2, the aforementioned pressure adjusting device 40 is configured in a general U-shape, and comprises a main unit 40a of which an interior has been filled with water, and a water sump unit 40b for receiving water with which the interior of the main unit 40a has been filled.

The aforementioned main unit 40a has a configuration wherein one end thereof is communicably connected to the aforementioned tube 14, and water from another end is received by the water sump unit 40b, and furthermore has a configuration wherein both legs of the main unit 40a can be slidably moved in a vertical direction so as to continuously press the water with which the interior thereof has been filled, thereby providing water within the needle 10 through the tube 14.

The pressure adjusting device 40 detects a change of pressure due to evaporation or the like as a change of pressure applied to the water with which the interior of the inserting opening 11 of the needle 10 has been filled, and adjusts a pressure applied to the interior of the inserting opening 11 by discharging water to the water sump 40b.

Here, while the aforementioned pressure due to evaporation is a pressure (positive pressure) higher than pressure within the inserting opening 11, and accordingly, pressure is adjusted by discharging water to the interior of the water sump unit 40b, in an event that vapor within the cavity is instantaneously cooled and liquefied due to continuous injection of the laser-absorbing medium or the like, and consequently, the pressure within the cavity becomes a pressure (negative pressure) lower than the pressure within the inserting opening 11, pressure at a time of laser irradiation is adjusted by sucking water, with which the interior of the water sump 40b has been filled, to the main unit 40a.

Thus, a required pressure can be adjusted for each diseased tissue at a time of laser beam irradiation, and also, there is an advantage in that in an event of an abnormal rising of vapor pressure occurring due to evaporation, pressure is guided out through the guide opening 13, thereby enabling abnormal thermal damage of the organic tissue to be prevented.

Figure 3:
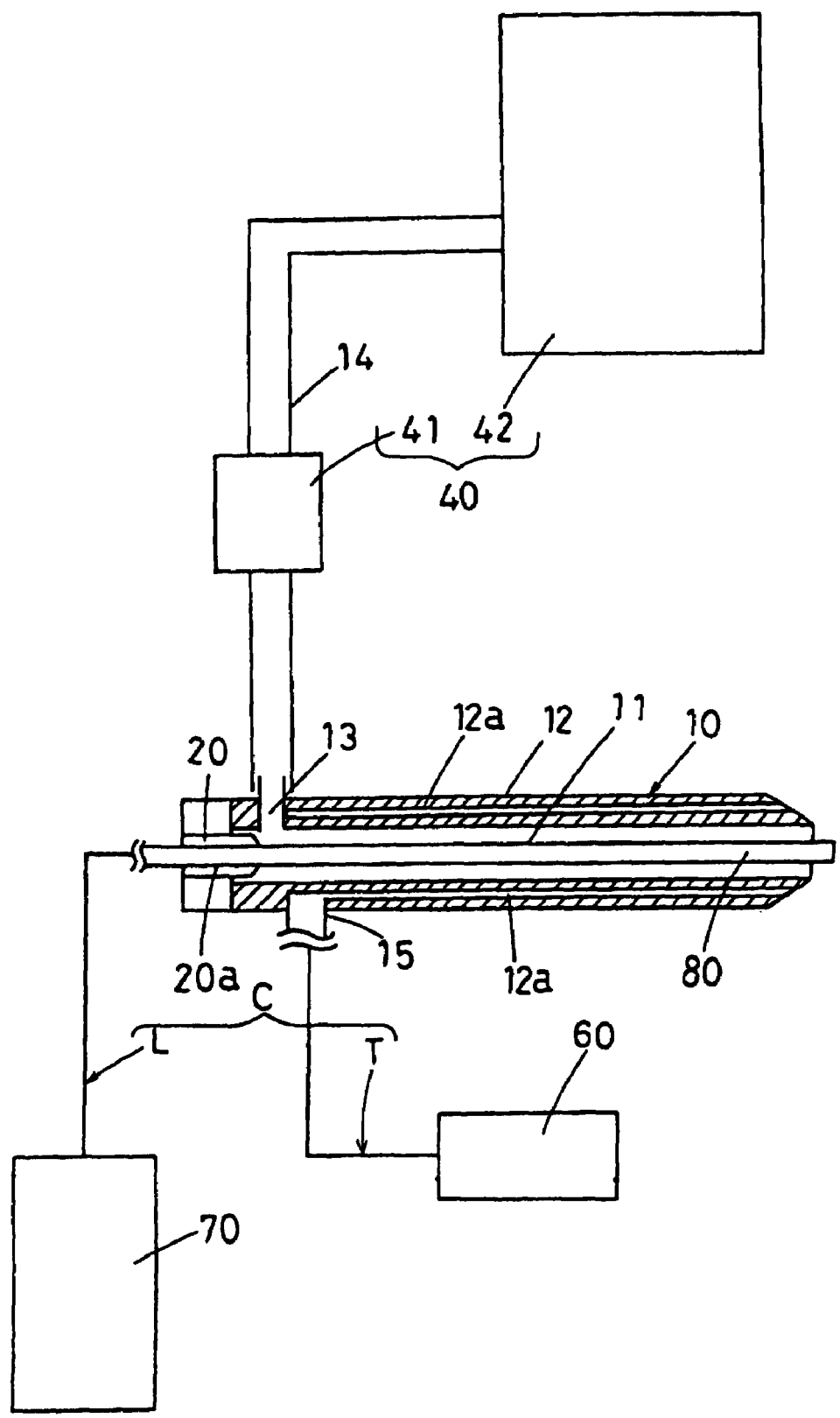
FIG. 3 is a configuration diagram which illustrates another further configuration of a laser treatment apparatus according to the present invention.

Also, as shown in FIG. 3, an arrangement may be made wherein the aforementioned pressure adjusting device 40 comprises a pressure sensor 41 and a pressure suction device 42.

In this case, one end of the pressure sensor 41 is communicably connected to the guide opening 13 of the aforementioned needle 10 through the tube 14, and another end is communicably connected to the pressure suction device 42.

Pressure within the inserting opening 11 of the needle 10 is detected by detecting a pressure within the tube 14 by the pressure sensor 41, and in an event of this detected value from the aforementioned pressure sensor 41 exceeding a predetermined value, the pressure suction device 42 is turned on so as to suck pressure within the inserting opening 11 through the tube 14, and also in an event that the pressure within the inserting opening 11 becomes a value equal to or less than a predetermined value, the pressure suction device 42 is stopped.

Figure 6C:
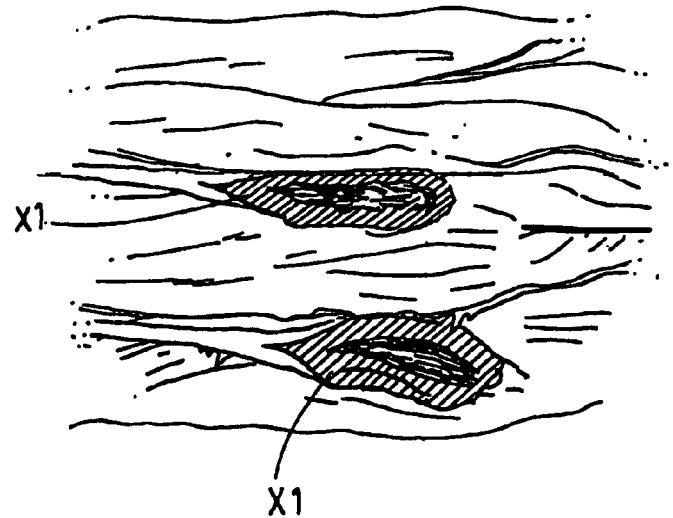

As a result, a required pressure for each diseased tissue can be adjusted at a time of laser beam irradiation in the same way as the above-described embodiment, and furthermore, unexpected thermal damage to organic tissue can be prevented in an event of an abnormal rising of vapor pressure occurring due to evaporation as shown in FIG. 6(c).

Note that FIG. 6(c) indicates that normal thermal damage X1 is caused to organic tissue due to performance of laser treatment, and thermal damage X2 is not caused to the organic tissue due to a backward flow of high-temperature vapor.

Furthermore, a needle for injecting a laser-absorbing medium into diseased tissue may have a configuration such as shown in FIGS. 7(a)–7(d).

Figure 7A:
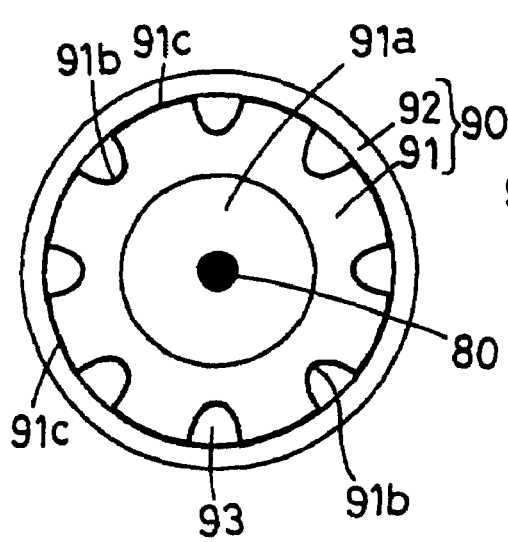
FIGS. 7(a)–7(d) show configuration diagrams which illustrate a configuration of a needle of the laser treatment apparatus according to the present invention.

That is to say, while with the above-described embodiment, the aforementioned needle includes the inserting opening 11 that passes through the needle along the axial direction from the front end up to the rear end thereof, and the outer tube 12 with a thickness, configured on an outer circumference of the aforementioned opening 11 in the shape of a tube, whereby the needle is configured in the shape of a tube, and multiple injecting openings 12a are provided in the outer tube 12 for injecting a laser-absorbing medium, a needle 90 according to the present embodiment comprises an inner tube 91 including an inserting opening 91a for inserting a laser fiber 80 of a laser beam irradiation device, and an outer tube 92 which is detachably mounted on the inner tube 91 as shown in FIG. 7(a).

The aforementioned inner tube 91 comprises the aforementioned inserting opening 91a generally at a central portion thereof, and further comprises multiple grooves 91b on an outer circumferential wall face thereof along an axial direction from a front end up to a rear end thereof, whereby the inner tube 91 is formed with a general cross-sectional shape of a gear, with multiple protrusions 91c on the outer circumferential wall face thereof adjacent to the aforementioned grooves 91b.

On the other hand, the outer tube 92, which is mounted on the inner tube 91, is formed in a cylindrical shape having a diameter of which an inner circumferential wall face is in contact with an outer circumferential wall face of the protrusions 91c provided on the outer circumferential wall of the above-described inner tube 91 with the inner tube 91 being mounted, and a locking mechanism (not shown) is provided at a rear end thereof for sealing and locking a gap between an outer circumferential wall of the rear end portion of the aforementioned inner tube 91 and an inner circumferential wall of the rear end portion of the outer tube 92 at the time of mounting the inner tube 91.

In an event of using the needle 90 having a configuration described above, first of all, a puncture needle (not shown) is mounted within the outer tube 92 for puncturing organic tissue. Here, the puncture needle corresponds to the inner tube 30 according to an above-described embodiment.

Thus, the needle 90 with the puncture needle being mounted is inserted into the organic tissue so as to reach diseased tissue, and subsequently, the inner tube 91 is mounted within the outer tube 92 of the needle 90, and also laser fiber 80 is inserted into the inserting opening 91a of the aforementioned inner tube 91 so as to cast a laser beam onto the diseased tissue which is an object of laser beam irradiation.

In this case, with the aforementioned needle 90, multiple injecting channels 93 are formed by the grooves 91b provided on the outer circumferential wall face of the inner tube 91 and the inner circumferential wall face of the outer tube 92, and are formed between the inner tube 91 and the outer tube 92, and accordingly, a laser-absorbing medium can be injected into the aforementioned injecting channels 93 so as to inject the laser-absorbing medium into diseased tissue which is an object of laser beam irradiation.

As a result, in an event of high-pressure vapor occurring due to evaporation from laser beam irradiation, this high pressure due to evaporation can be vented from the inserting opening 20a of the seal member 20 provided to at rear end portion of the needle 90, and also, even in an event of a backward flow of high-temperature vapor occurring within the inserting opening 91a of the needle 90, laser-absorbing medium continuously flows into the injecting channels 93 of the needle 90, and accordingly, the needle 90 itself is cooled, thereby enabling thermal damage of the needle 90 or the laser fiber 80, due to the vapor, to be prevented, in the same way as with the above-described embodiments. Thus, there is also an advantage of preventing burns from occurring on organic tissue around the needle 90.

Furthermore, the aforementioned inner tube 91 and the outer tube 92 are mounted with the gap between the outer circumferential wall and the inner circumferential wall being sealed and locked, so vapor due to evaporation does not leak from the gap between the inner tube 91 and the outer tube 92, and furthermore, the outer tube 92 is mounted on the inner tube 91 in a locked manner, and accordingly, the laser fiber 80 inserted into the inserting opening 91a of the inner tube 91 is disposed within the inserting opening 91a in a stabilized manner.

Moreover, with the above-described embodiment, the needle can be easily formed as compared with a case wherein multiple injecting openings 12a are provided in the outer tube 12 for injecting a laser-absorbing medium, and thus, there is an advantage of reducing costs.

Figure 7B:
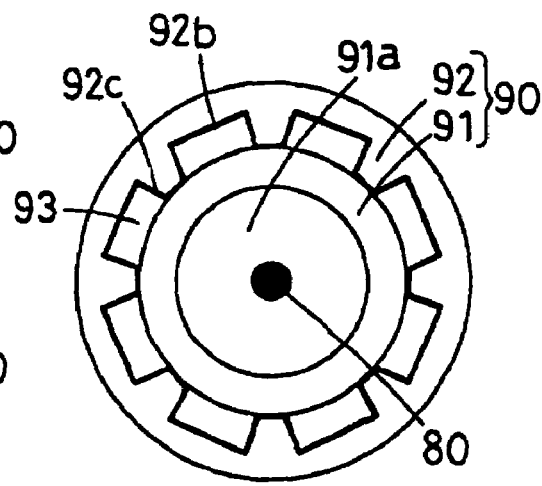

While multiple grooves are provided in the outer circumferential wall face of the inner tube 91 with the above-described embodiment, an arrangement may be made wherein multiple grooves 92b are provided in the inner circumferential face of the outer tube 92 as shown in FIG. 7(b) so that the outer tube 92 is formed having a structure wherein multiple protrusions 92c are provided adjacent to the grooves 92b of the inner circumferential wall face, and the inner circumferential wall face of the aforementioned outer tube 92 is pressed into contact with the outer circumferential wall of the inner tube 91 so as to form the injecting channels 93 for injecting a laser-absorbing medium.

In this case, in an event of high-pressure vapor occurring due to evaporation by laser beam irradiation, this high pressure due to evaporation also can be vented from the inserting opening 20a of the seal member 20 of the aforementioned needle 90, and furthermore, even in an event of a backward flow of high-temperature vapor occurring within the inserting opening 91a of the needle 90, laser-absorbing medium continuously flows into the injecting channels 93 of the aforementioned needle 90, so the needle 90 itself is cooled, thereby enabling thermal damage of the needle 90 or the laser fiber 80 due to evaporation to be prevented, in the same way as with the above-described embodiments. Moreover, this yields an advantage of preventing burns from occurring on organic tissue around the needle 90.

The laser treatment apparatus is not intended to be restricted to the above-described embodiments, but rather, various modifications may be made within the scope of the claims. That is to say, the needle may have any configuration so long as the needle includes an inserting opening for inserting a light guide member, and also includes injecting channels for injecting a laser-absorbing medium, and the aforementioned injecting channels are provided in a portion with a thickness between an outer circumference of the aforementioned inserting opening and an outer circumference of the needle, and the injecting channels are connected to a syringe pump through a connecting portion of the needle.

Figure 7C:
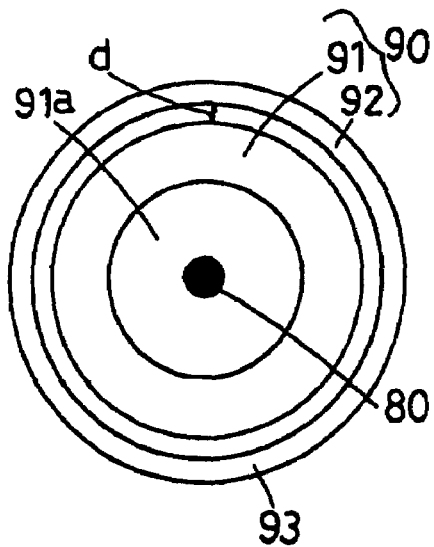

For example, the needle may have a configuration shown in FIG. 7(c). In this case, needle 90 comprises inner tube 91 including inserting opening 91a, and outer tube 92 which can be detachably mounted on the inner tube 91, in the same way as the above-described embodiments.

A diameter of an outer circumferential wall of the inner tube 91, and a diameter of an inner circumferential wall of the outer tube 92, are determined so as to generate a gap with a predetermined thickness d with the inner tube 91 being mounted within the outer tube 92. Accordingly, the gap forms an injecting channel for injecting a laser beam injecting medium.

Thus, while injecting the laser-absorbing medium into diseased tissue, which is an object of laser beam irradiation, from the injecting channel with the aforementioned gap, laser beam irradiation is performed, whereby the same advantages can be obtained as with the above-described embodiments.

Also, an arrangement may be made wherein, with the needle where the predetermined gap of thickness d is provided between the inner tube 91 and the outer tube 92 described above, a front end portion of the outer tube 92 is bent toward a central portion of the tube so that the front end portion covers over a front end portion of the inner tube 91 through the aforementioned thickness d, and multiple small openings are formed in this bent portion of the outer tube 92 so as to form an injecting channel for injecting a laser-absorbing medium, made up of the gap between the aforementioned inner tube 91 and the outer tube 92, and the aforementioned small openings.

Note that in this case, a puncture needle, which is mounted within the outer tube 92 in an event of puncturing organic tissue, has a diameter and structure which enables the puncture needle to be mounted in the outer tube 92.

In this case, the same advantages also can be obtained as with the above-described embodiments.

Figure 7D:
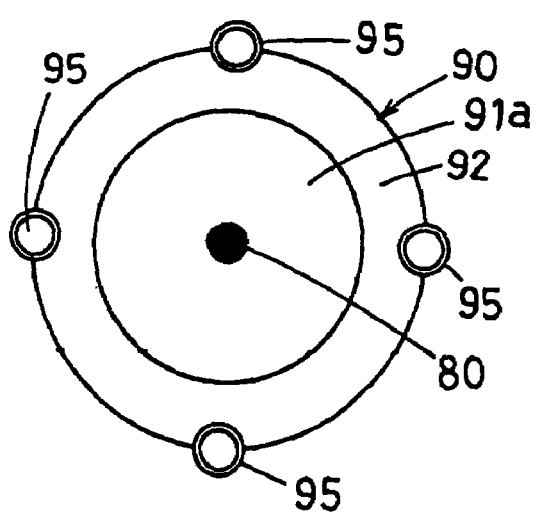

Furthermore, an arrangement may be made wherein multiple medium-injecting needles 95, including injecting openings for injecting a laser-absorbing medium, are mounted as separated units on an outer circumferential wall face of outer tube 92 of needle 90 including inserting opening 91a as shown in FIG. 7(d), whereby a needle of the laser treatment apparatus according to the present invention is configured.

In this case, "needle" means an overall needle with the medium-injecting needles 95 being mounted, and "outer circumference of the needle" means an outer circumference of the outer tube 92 of the needle 90 including outer circumferences of the medium-injecting needles 95.

Thus, with the laser treatment apparatus including the needle having a configuration described above, a laser-absorbing medium is injected into diseased tissue, which is an object of laser beam irradiation, from injecting openings provided in the medium-injecting needles 95, and laser beam irradiation is performed using laser fiber 80 inserted into the inserting opening 91a, whereby the same advantages also can be obtained as with the above-described embodiments.

Figure 8:
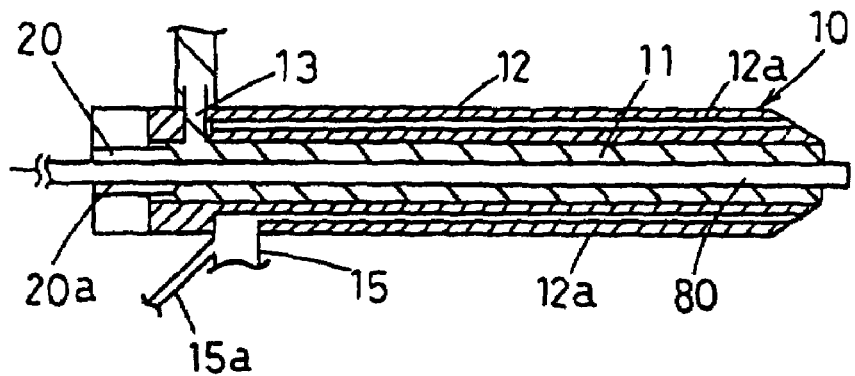
FIG. 8 is a configuration diagram which illustrates a configuration of a needle of the laser treatment apparatus according to the present invention.

Furthermore, as shown in FIG. 8, an arrangement may be made wherein a tube (injecting channel) 15a is communicably connected to connecting portion 15 of needle 10 according to the present invention so as to configure a gas injecting device for injecting gas, and gas is injected along with a laser-absorbing medium externally into injecting opening 12a that passes through the needle 10 along an axial direction from a front end up to a rear end thereof. In this case, carbon dioxide, nitrogen, helium, or the like, is used as the aforementioned gas which is to be injected, for example.

Upon casting a laser beam onto diseased tissue, which is an object of laser beam irradiation, using the needle 10 having a configuration as described above, a laser-absorbing medium injected to the diseased tissue is diffused as a mist and sprayed under pressure of gas which has been separately injected, and thus the laser-absorbing medium can reach a further and wider range of the diseased tissue.

As a result, a quantity of the laser-absorbing medium which does not reach the diseased tissue, and accordingly does not contribute to evaporation of the diseased tissue which is the object of laser beam irradiation, is reduced, and evaporation of the diseased tissue can be efficiently effected in a sure manner, thereby enabling great evaporation of the diseased tissue to be obtained without increasing an output of laser beam irradiation.

Note that, while the above-described tube 15a as an injecting channel for injecting gas is configured to be communicably connected to the connecting portion 15, the injecting channel may be provided at any portion of the needle 10 so long as the injecting channel is communicably connected to the inserting opening 12a of the needle 10.

Also, an arrangement may be made wherein the above-described injecting channel for injecting gas is provided in the needle 90.

INDUSTRIAL APPLICABILITY

According to the present invention, a laser treatment method has a configuration wherein a laser-absorbing medium is injected between diseased tissue, which is an object of laser irradiation, and a laser beam output end, and a laser beam is cast onto the aforementioned laser-absorbing medium so as to cause thermal damage such as evaporation or coagulation of the diseased tissue which is the object of laser irradiation, and thus thermal damage such as evaporation or necrosis due to coagulation can be caused to the tissue, which is to be subjected to thermal damage, in a sure manner regardless of an absorption percentage for the laser beam due to a color tone or composition of this organic tissue.

Furthermore, the laser treatment method according to the present invention is configured so as to vent pressure externally in an event of an abnormal pressure occurring due to evaporation of diseased tissue, thereby enabling harmful effects such as diffusion of cancer cells or the like, due to the abnormal pressure, to be prevented.

With the laser treatment method according to the present invention, a laser-absorbing medium can be injected into diseased tissue, which is an object of laser irradiation, by a single injection or in a continuous manner, and accordingly, injection of the laser-absorbing medium can be performed in accordance with the diseased tissue. In particular, in an event of continuous injection, the laser-absorbing medium is continuously injected, and becomes a heat source between the diseased tissue and a laser fiber, thereby enabling a cavity to be expanded, and thermal damage of surrounding tissue to be effected.

Furthermore, according to the present invention, the laser treatment method has a configuration wherein a laser-absorbing medium is injected with laser output, administrating quantity of heat, and injecting speed thereof being controlled according to a size or shape of diseased tissue which is an object of laser irradiation, thereby enabling a degree of thermal damage applied to the diseased tissue, which is the object of laser beam irradiation, to be controlled.

On the other hand, the laser-absorbing medium used in the above-described laser treatment may employ diluted blood from a patient, an indocyanine green solution (ICG), or a solution wherein human serum has been added into an indocyanine green solution (ICG), or a solution wherein indocyanine green is dissolved in distilled water, and accordingly, an administrating quantity of heat can be controlled, thereby enabling effective laser treatment according to an object of a treatment to be performed.

According to the present invention, a laser treatment apparatus has a configuration wherein a laser-absorbing medium stored in a syringe pump is injected into diseased tissue, which is an object of laser beam irradiation, with a needle, and a laser beam is cast onto the aforementioned laser-absorbing medium by guiding the laser beam with a light guide member so as to cause thermal damage such as evaporation or coagulation of the aforementioned diseased tissue which is the object of laser beam irradiation, and thus, thermal damage such as evaporation or necrosis due to coagulation can be caused to the tissue, which is to be subjected to thermal damage, in a sure manner regardless of an absorption percentage of the laser beam due to a color tone or composition of this organic tissue.

Furthermore, with the laser treatment apparatus according to the present invention, a light guide member is inserted into an inserting opening of a needle, and also a laser-absorbing medium is injected into diseased tissue, which is an object of laser beam irradiation, from an injecting channel provided in the needle, and laser beam irradiation is performed, and in an event of high-pressure vapor occurring due to evaporation from irradiation of the laser beam, the aforementioned high-pressure vapor is vented within the inserting opening, and also, even in an event of a backward flow of high-temperature vapor occurring within the inserting opening of the needle, the laser-absorbing medium flows into the injecting channel which has been provided separately from the aforementioned inserting opening of the needle, so the needle itself is cooled, thereby enabling thermal damage of the needle or the light guide member due to the vapor to be prevented.

Moreover, this yields an advantage of preventing burns from occurring on organic tissue around the needle.

With the laser treatment apparatus according to the present invention, a seal member is provided with an inserting opening for inserting a light guide member, and the light guide member is inserted into the inserting opening of a needle through the aforementioned inserting opening, and accordingly, some degree of pressure can be kept within the inserting opening of the needle by the aforementioned seal member, and furthermore, in an event of high-pressure vapor occurring due to evaporation by laser beam irradiation, this high pressure due to evaporation can be vented from the inserting opening of the aforementioned seal member of the needle.

With the laser treatment apparatus according to the present invention, injecting channels for injecting the aforementioned laser-absorbing medium are made up of an inner circumferential wall face of an outer tube and grooves on an outer circumferential wall face of the inner tube, and accordingly, a needle can be easily formed, and thus, there is an advantage of reducing costs thereof.

With the laser treatment apparatus according to the present invention, in an event of high-pressure vapor occurring due to evaporation by laser beam irradiation, this high pressure due to evaporation can be detected and vented from a guide portion, and thus, there is an advantage of preventing unexpected thermal damage to organic tissue.

Furthermore, a required pressure can be adjusted for each diseased tissue at a time of laser beam irradiation.

Moreover, a laser-absorbing medium which is to be injected into diseased tissue is diffused as a mist and sprayed under pressure of gas which has been separately injected, and accordingly, the laser-absorbing medium can reach a further and wider range of the diseased tissue, and thus, a quantity of the laser-absorbing medium which does not reach the diseased tissue and accordingly does not contribute to evaporation of the diseased tissue, which is an object of laser beam irradiation, is reduced, and evaporation of the diseased tissue can be efficiently effected in a sure manner. Moreover, this allows great evaporation of the diseased tissue to be obtained without increasing an output of a laser.

The invention claimed is:

1. A laser treatment method comprising:
    injecting a laser beam absorption medium between diseased tissue, of a patient, and a laser beam output end; and
    casting a laser beam onto said laser beam absorption medium so as to cause thermal damage to said diseased tissue,
    wherein said laser beam absorption medium comprises diluted blood from the patient.

2. The laser treatment method according to claim 1, wherein
    casting a laser beam onto said laser beam absorption medium so as to cause thermal damage to said diseased tissue comprises casting said laser beam onto said laser beam absorption medium so as to cause at least one of evaporation and coagulation of said diseased tissue.

3. The laser treatment method according to claim 1, further comprising:
    when an abnormal pressure occurs due to the thermal damage caused to said diseased tissue, externally venting the abnormal pressure.

4. The laser treatment method according to claim 3, wherein
    casting a laser beam onto said laser beam absorption medium so as to cause thermal damage to said diseased tissue comprises casting said laser beam onto said laser beam absorption medium so as to cause at least one of evaporation and coagulation of said diseased tissue,
    such that externally venting the abnormal pressure comprises venting an abnormal pressure resulting when evaporation of said diseased tissue is caused.

5. The laser treatment method according to claim 1, wherein
    injecting a laser beam absorption medium between diseased tissue and a laser beam output end comprises performing a single injection of said laser beam absorption medium between said diseased tissue and said laser beam output end.

6. The laser treatment method according to claim 1, wherein
injecting a laser beam absorption medium between diseased tissue and a laser beam output end comprises continuously injecting said laser beam absorption medium between said diseased tissue and said laser beam output end.

7. A laser treatment method comprising:
continuously injecting a laser beam absorption medium between diseased tissue and a laser beam output end; and
casting a laser beam onto said laser beam absorption medium so as to cause thermal damage to said diseased tissue,
wherein said laser beam absorption medium comprises a solution including human serum and an indocyanine green solution.

8. The laser treatment method according to claim 7, wherein
casting a laser beam onto said laser beam absorption medium so as to cause thermal damage to said diseased tissue comprises casting said laser beam onto said laser beam absorption medium so as to cause at least one of evaporation and coagulation of said diseased tissue.

9. The laser treatment method according to claim 7, further comprising:
when an abnormal pressure occurs due to the thermal damage caused to said diseased tissue, externally venting the abnormal pressure.

10. The laser treatment method according to claim 9, wherein
casting a laser beam onto said laser beam absorption medium so as to cause thermal damage to said diseased tissue comprises casting said laser beam onto said laser beam absorption medium so as to cause at least one of evaporation and coagulation of said diseased tissue,
such that externally venting the abnormal pressure comprises venting an abnormal pressure resulting when evaporation of said diseased tissue is caused.

11. A laser treatment apparatus comprising:
a medium injecting device for injecting a laser beam absorption medium into diseased tissue, which is to be an object of laser irradiation, said medium injecting device including
  (i) a needle having
    (a) an inserting opening passing through said needle along an axial direction from a front end to a rear end of said needle,
    (b) a guide portion at said rear end portion of said needle communicably connected to said inserting opening for guiding pressure from within said inserting opening to outside said needle, and
    (c) an injecting channel defined in a wall of said needle and passing therethrough, along the axial direction from the front end to the rear end of said needle, between an outer circumference of said inserting opening and an outer circumference of said needle, and
  (ii) a syringe pump for storing therein the laser beam absorption medium, with said injecting channel being communicably connected to said syringe pump via a connecting portion at a rear end portion of said needle;
a laser beam irradiation device for casting a laser beam onto the diseased tissue into which the laser beam absorption medium has been injected, said laser beam irradiation device including a light guide member for guiding the laser beam from a laser beam irradiation member to the diseased tissue;
a detecting device for detecting pressure within said inserting opening; and
a pressure adjusting device for adjusting pressure within said inserting opening by guiding the pressure externally from said guide portion according to the pressure as detected by said detecting device,
wherein said inserting opening is for having received therein said light guide member.

12. A laser treatment apparatus comprising:
a medium injecting device for injecting a laser beam absorption medium into diseased tissue, which is to be an object of laser irradiation, said medium injecting device including
  (i) a needle having
    (a) an inserting opening passing through said needle along an axial direction from a front end to a rear end of said needle, and
    (b) an injecting channel defined in a wall of said needle and passing therethrough, along the axial direction from the front end to the rear end of said needle, between an outer circumference of said inserting opening and an outer circumference of said needle, and
  (ii) a syringe pump for storing therein the laser beam absorption medium, with said injecting channel being communicably connected to said syringe pump via a connecting portion at a rear end portion of said needle;
a laser beam irradiation device for casting a laser beam onto the diseased tissue into which the laser beam absorption medium has been injected, said laser beam irradiation device including a light guide member for guiding the laser beam from a laser beam irradiation member to the diseased tissue; and
a gas injecting device, communicably connected to said injecting channel, for externally injecting gas into said injecting channel,
wherein said inserting opening is for having received therein said light guide member.

13. A laser treatment method comprising:
injecting a laser beam absorption medium between diseased tissue and a laser beam output end;
casting a laser beam onto said laser beam absorption medium so as to cause thermal damage to said diseased tissue;
controlling an output of said laser beam, an administrating quantity of heat, and an injecting speed of said laser beam absorption medium, corresponding to a size or shape of said diseased tissue; and
when an abnormal pressure occurs due to the thermal damage caused to said diseased tissue, externally venting the abnormal pressure.

14. The laser treatment method according to claim 13, wherein
casting a laser beam onto said laser beam absorption medium so as to cause thermal damage to said diseased tissue comprises casting said laser beam onto said laser beam absorption medium so as to cause at least one of evaporation and coagulation of said diseased tissue,
such that externally venting the abnormal pressure comprises venting an abnormal pressure resulting when evaporation of said diseased tissue is caused.

* * * * *